United States Patent
Lieb et al.

(10) Patent No.: US 9,877,798 B2
(45) Date of Patent: Jan. 30, 2018

(54) ELECTRIC DENTAL HANDPIECE

(71) Applicants: Spring Health Products, Inc., Norristown, PA (US); Joseph A. Lieb

(72) Inventors: Joseph A. Lieb, Philadelphioa, PA (US); Nathaniel H. Lieb, Narberth, PA (US); Arthur A. Knopp, Chalfont, PA (US)

(73) Assignee: SPRING HEALTH PRODUCTS, INC., Norristown, PA (US)

( * ) Notice: Subject to any disclaimer, the term of this patent is extended or adjusted under 35 U.S.C. 154(b) by 872 days.

(21) Appl. No.: 13/683,223

(22) Filed: Nov. 21, 2012

(65) Prior Publication Data

US 2013/0203014 A1    Aug. 8, 2013

Related U.S. Application Data

(63) Continuation-in-part of application No. 11/871,394, filed on Oct. 12, 2007, now abandoned, which is a continuation of application No. PCT/US2006/013345, filed on Apr. 11, 2006.

(60) Provisional application No. 60/670,584, filed on Apr. 12, 2005.

(51) Int. Cl.
| | |
|---|---|
| A61C 1/00 | (2006.01) |
| A61C 1/06 | (2006.01) |
| A61C 1/18 | (2006.01) |
| A61C 17/02 | (2006.01) |
| A61C 1/12 | (2006.01) |
| A61C 1/05 | (2006.01) |

(52) U.S. Cl.
CPC .............. *A61C 1/06* (2013.01); *A61C 1/0015* (2013.01); *A61C 1/12* (2013.01); *A61C 1/185* (2013.01); *A61C 17/02* (2013.01); *A61C 1/052* (2013.01); *A61C 17/0217* (2013.01)

(58) Field of Classification Search
CPC ........... A61C 1/06; A61C 1/0015; A61C 1/12; A61C 1/185; A61C 17/02; A61C 1/052; A61C 17/0217
USPC ................................ 433/104, 131, 114, 126
See application file for complete search history.

(56) References Cited

U.S. PATENT DOCUMENTS

| | | | |
|---|---|---|---|
| 3,487,546 A * | 1/1970 | Beierlein | 433/104 |
| 4,007,529 A * | 2/1977 | Fleer | 433/104 |
| 4,534,734 A * | 8/1985 | Lares | 433/126 |
| 5,079,488 A * | 1/1992 | Harms et al. | 318/471 |
| 5,510,687 A * | 4/1996 | Ursworth et al. | 318/727 |
| 5,846,078 A * | 12/1998 | Rosenstatter | 433/132 |
| 5,944,523 A * | 8/1999 | Badoz | 433/131 |
| 6,033,220 A * | 3/2000 | Mosimann | 433/126 |
| 6,607,384 B1 * | 8/2003 | Nakanishi | 433/29 |
| 2003/0190583 A1 * | 10/2003 | Kuhn | 433/131 |

* cited by examiner

*Primary Examiner* — Heidi M Eide
(74) *Attorney, Agent, or Firm* — Massina Pat. & TM Law PLLC

(57) ABSTRACT

An electric dental handpiece including a head engaging a handle and configured to rotatably support a tool. The handle includes a lower handle portion and an upper handle portion with the lower handle portion engaging the head and the upper handle portion having an attachment area configured for attachment to a power supply. An electric motor is positioned with a majority thereof within the lower handle portion and is configured to rotate the tool.

22 Claims, 15 Drawing Sheets

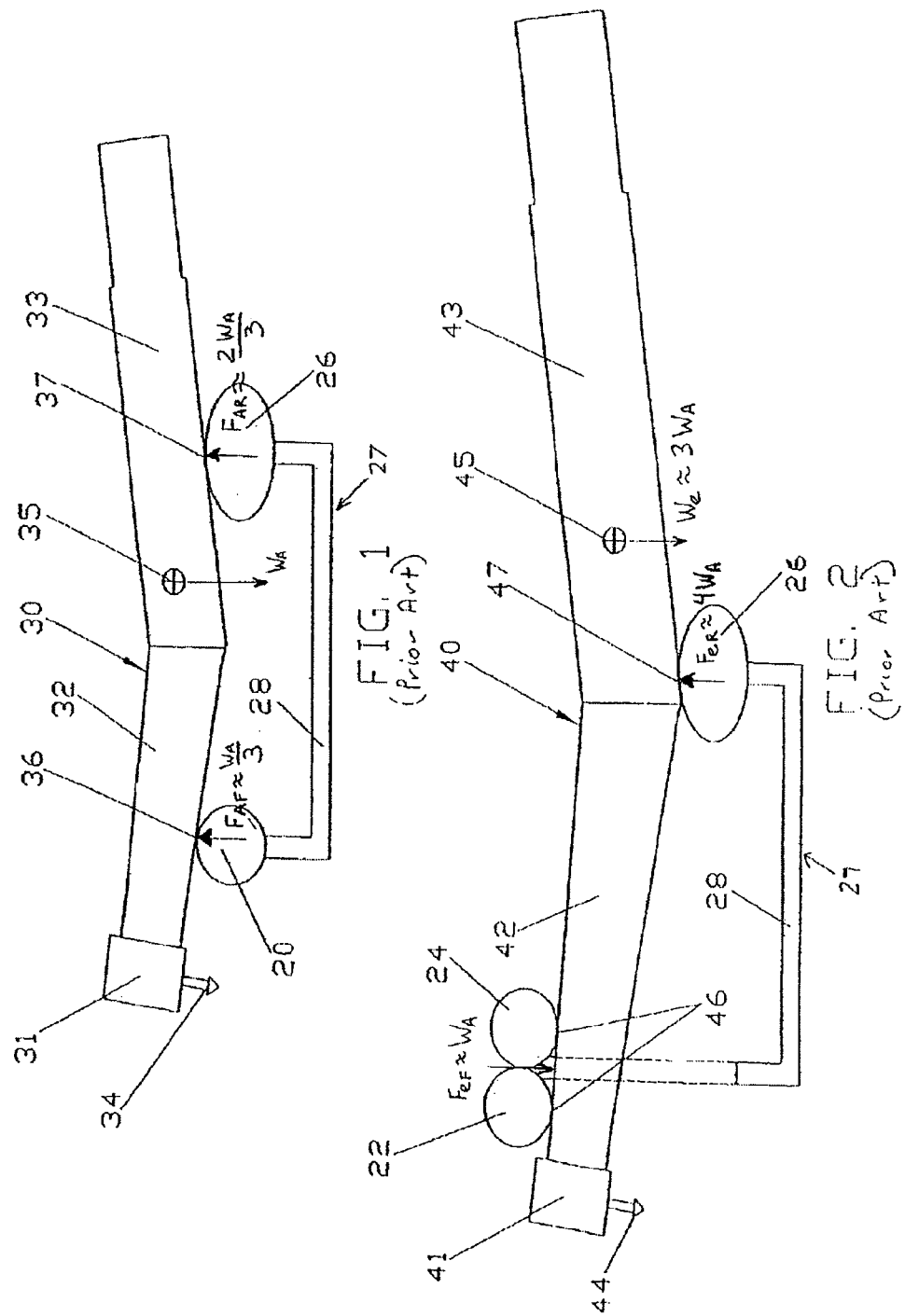

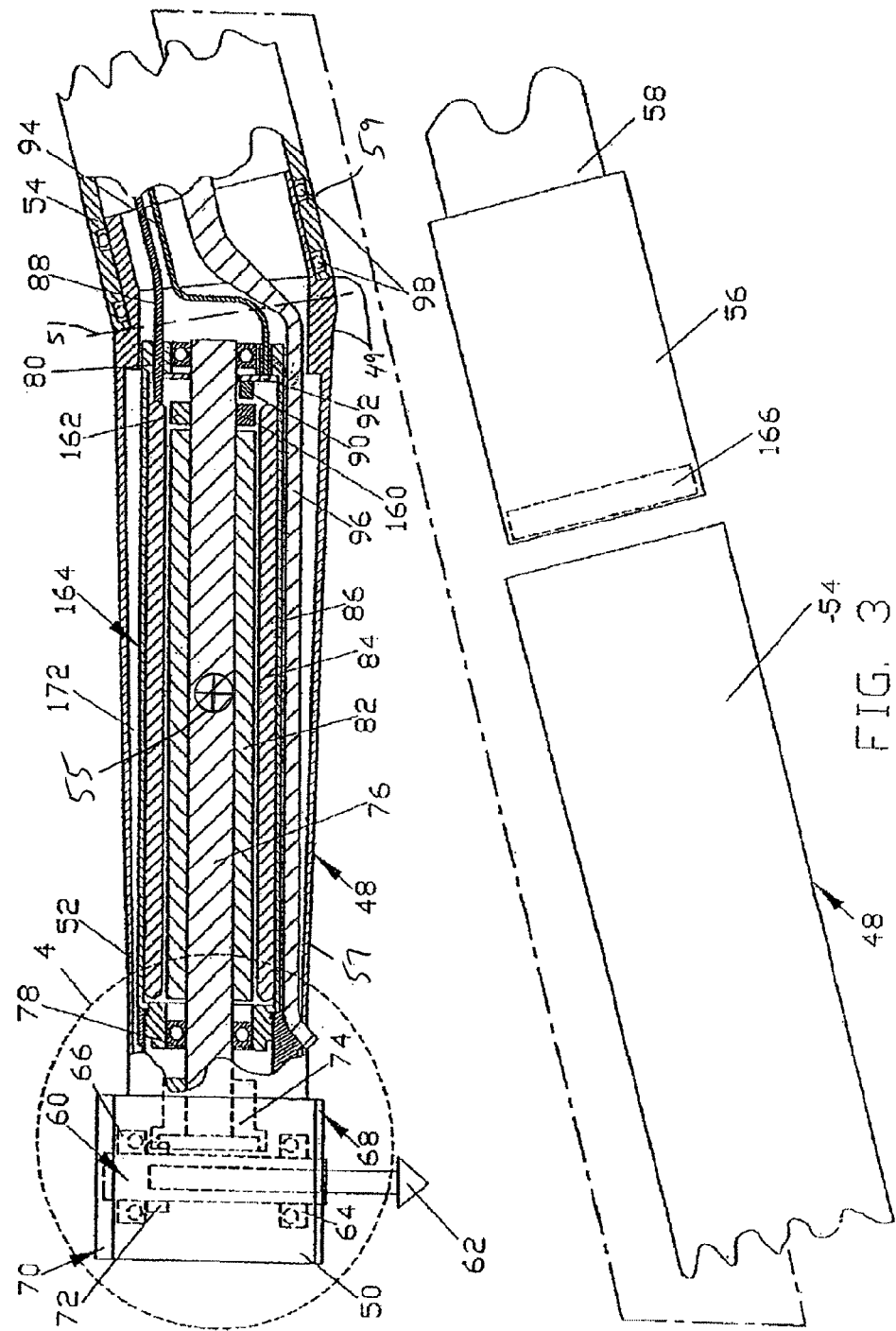

1

ELECTRIC DENTAL HANDPIECE

This application is a continuation-in-part of U.S. patent application Ser. No. 11/871,394, filed on Oct. 12, 2007, which is a continuation of PCT International Application No. PCT/US2006/013345, filed on Apr. 11, 2006, which claims the benefit of U.S. Provisional Application No. 60/670,584, filed on Apr. 12, 2005, each of which is incorporated herein by reference.

BACKGROUND OF THE INVENTION

The present invention relates to electric motor powered dental handpieces. More particularly, the present invention relates to an electric motor powered dental handpiece that utilizes an electric motor to directly drive a spindle chucking assembly that holds a desired tool.

Electric handpieces are currently being marketed. Electric motor driven dental handpieces are described in U.S. Pat. No. 4,278,429 to Straihammer et al.; U.S. Pat. No. 4,355,977 to Ota et al. and U.S. Pat. No. 4,486,176 to Tardieu et al. In some aspects, electric powered handpieces have advantages over air powered models, for example, electric powered handpieces exhibit superior speed regulation; provide an acceptable degree of speed regulation over a wide range of desired outputs speeds; and the torque that is supplied, particularly at lower speeds, is excellent. However, prior art electric powered handpieces have several disadvantages compared to air driven handpieces, including: increased weight; larger diameter and length; difficult or impossible to service in the dental office; lack of a fiber optic swivel; and price.

More specifically, currently marketed electric handpiece systems and their associated motors are approximately three times the weight of air handpieces. A significant amount of the additional weight is concentrated at the rear end of the electric handpiece handle. In some designs, the motor is physically located in the dental hose connection area which attaches to the rear portion of the handpiece handle. Most of the weight is due to the electric motor. The electric motor length of currently marketed electric handpiece systems causes the electric handpiece and attached hose connection combined length to be about 40% longer than the air handpiece length. Similarly, the motor diameter causes the electric handpiece diameter (in the area where the motor is located) to be about 30% larger than the maximum diameter of an air handpiece.

The additional weight of the electric motor and its location, significantly away from the head (where the cutting tool is chucked), combine to make electric handpieces awkward and tiring to use. The center of gravity of these electric handpieces are located beyond the normal gripping range of the dentist's hand.

A dentist basically grips a dental handpiece as one would grip a pencil while writing. The gripping range of a dentist's hand is comprised of two different types of grips separated by a distance. The gripping range begins with a combined "three finger grip" placed at the front of a handpiece. The area gripped is the lower handle portion of the handpiece and is located very closely to the head of the handpiece. The head contains the spindle assembly which is designed to rotate at a broad range of speeds. Variously shaped cutting tools can be mounted or "chucked" in the spindle to perform a variety of cutting procedures. The tips of the thumb, index finger and middle finger are oriented to surround the front portion of the handle in order to precisely locate the cutting tool. The gripping range ends with a "cradle" type of grip generated by the "crook" area of the dentist's hand that is placed under the rear portion of the handpiece handle. The physical distance between the front and rear grips is referred to herein as the "gripping span."

FIG. 1 illustrates a force distribution diagram of a typical air powered handpiece 30 when gripped by a simulated dentist's hand 27. The air handpiece 30 generally consists of a head 31 which is fastened to a handle comprised of a lower handle portion 32 and an upper handle portion 33. The head 31 contains an air turbine (not shown) which rotates a cutting tool 34 at a high speed. The center of gravity 35 represents the approximate location at which the total weight "$W_A$" of air handpiece 30 can be considered to be concentrated for weight distribution analysis. Reference numbers 20, 26 and 28 represent simulated segments of a dentist's hand 27. The lower handle portion 32 is primarily supported at front gripping area 36 by the dentist's middle finger 20. The upper handle portion 33 is supported at rear gripping area 37 by the crook area 26 of the dentist's hand 27. Gripping span 28 indicates the relative anatomical distance between middle finger 20 and crook 26 of the dentist's hand 27.

A typical air handpiece 30 weighs about 50 grams. When the air handpiece 30 is held by a dentist, its center of gravity 35 occurs within the dentist's gripping span. The actual location of the center of gravity 35 occurs at an upper handle portion 33 location which is approximately twice as far from the three finger grip at the front gripping area 36 as it is from the crook area 26 at the rear gripping area 37. The weight distribution is therefore about ⅓ ($F_{AF} \approx W_A/3$) at the front gripping area 36 and ⅔ ($F_{AR} \approx 2W_A/3$) at the rear griping area 37. This computes to approximately 17 grams at the front gripping area 36 and 33 grams at the rear gripping area 37. A closer analysis of the weight distribution at the front gripping area 36 reveals that the 17 gram weight is virtually completely supported by the side of the middle finger 20. The thumb (not shown) and index finger (not shown) are used mainly to provide a very light lateral stabilizing force during actual cutting procedures.

The direction of the forces $F_{AF}$ and $F_{AR}$ created by the weight of the air handpiece 30 at the front gripping area 36 and rear gripping area 37, respectively, is downward in both cases. Having handpiece forces $F_{AF}$ and $F_{AR}$ oriented in a downward direction at the front and rear gripping areas of the dentist's hand 27 may not appear to be a significant advantage, however this configuration, which results from an air handpiece 30 having a center of gravity 35 located between the front gripping area 36 and rear gripping area 37, is desirable because it allows the front grip to be made with substantially less effort, compared to that required by the currently marketed electric powered handpieces, as will be described hereinafter.

FIG. 2 illustrates a force distribution diagram of a typical currently available electric handpiece 40 when gripped by a simulated dentist's hand 27. The electric handpiece 40 generally consists of a head 41 which is fastened to a handle 49 comprised of a lower handle portion 42 and an upper handle portion 43. The lower handle portion 42 and the upper handle portion 43 refer to general areas of the handle 49. Throughout the following text, in general, the lower handle portion 42 of our invention is considered to be the section of the handle 49 that is forward (toward the head 41) of the rear gripping area 47 of the handle 49. The upper handle portion 43 is considered to be the section of the handle that is rearward (away from the head 41) of the rear gripping area 47 of the handle 49. The handle 49 does not have to be comprised of two physical sections. It could be comprised of a single continuous piece of material or could be comprised of three or more sections of material. If the handle is constructed of two pieces, the mating plane 51 can occur at any place in the handle 49 assembly and not necessarily as illustrated in FIG. 3.

The head 41 contains a spindle chucking assembly (not shown) which rotates a cutting tool 44. The center of gravity 45 represents the approximate location at which the total weight "$W_e$" of electric handpiece 40 can be considered to be concentrated for weight distribution analysis. Reference numbers 22, 24, 26 and 28 represent simulated segments of the dentist's hand 27. The lower handle portion 42 is primarily gripped at front gripping area 46 by index finger 22 and thumb 24. The upper handle portion 43 is supported at the rear gripping area 47 by crook area 26 of a dentist's hand 27. Gripping span 28 simulates the relative anatomical distance between front gripping area 46, which is gripped by index finger 22 and thumb 24, and the crook area 26.

The threefold weight factor of electric versus air models and the weight distribution of typical current electric handpieces 40 require substantially more gripping effort to be supplied by the dentist. The center of gravity 45 of a typical electric handpiece 40 is located significantly farther from the head 41. The center of gravity 45 of electric handpiece 40 lies outside the typical hand gripping range described above. It lies about ⅓ of the "gripping span" distance beyond the crook area 26. A force distribution of an electric handpiece 40, assuming a weight of about 150 grams, results in a 50 gram force $F_{eF}$ at the front gripping area 46 and a 200 gram force $F_{eR}$ at the rear gripping area 47. The force $F_{eF}$ required to support the electric handpiece 40 at the front gripping area 46 is approximately three times what was necessary to support the air handpiece 30 at its front gripping area 36 ($F_{eF} \approx W_A \approx 3F_{AF}$). Additionally, the front gripping force $F_{eF}$ must be supplied in a downward direction for the electric handpiece 40. The rear gripping force $F_{eR}$ required to support electric handpiece 40 at the rear gripping area 47 or crook 26 area, is approximately six times that required to support air handpiece 30 at the same location ($F_{eR} \approx 4W_A \approx 6F_{AR}$).

The downward direction and magnitude of the front gripping force $F_{eF}$ required to support electric handpiece 40 requires significantly more effort by the dentist. The thumb 24 and index finger 22 are still required to provide lateral stabilizing force during actual cutting procedures. However, in addition to providing lateral stabilizing forces, the thumb 24 and index finger 22 must also provide a downward force $F_{eF}$. This force of about 50 grams is approximately three times as much as the upward force exerted by the middle finger 20 for an air handpiece 30. The middle finger (not shown on FIG. 2) is only very lightly used to support electric handpiece 40.

The approximate six fold increase in force $F_{eR}$ required at the rear gripping area 47 by the crook 26 area to support electric handpiece 40 compared to air handpiece 30, is one of the reasons why currently marketed electric handpieces are not particularly favored by dentists.

There is a related problem caused by the weight distribution of electric handpieces. Frequently a dentist will be gripping a handpiece, but he will not be using it to remove tooth material. For example, the dentist will not be using a handpiece to remove tooth material when he needs to view the progress of his work, to reposition the cutting tool or to install a new cutting tool. During these periods, the dentist will typically relax his grip on the handpiece to minimize fatigue. Because the air handpiece 30 is significantly lighter and because the air handpiece force is directed downward for both the front gripping area 36 and rear gripping area 37, the dentist can relax his grip significantly without any serious consequences. The thumb and index grips can almost be completely eliminated without any problems. However if the same type of relaxed grip is attempted with the front grip of electric handpiece 40, the front of electric handpiece 40 will rise and the electric handpiece 40 will slip out of the dentist's hand 27. Because the dentist's hand is usually very wet, it is possible for an accidental or unplanned reduction of front gripping force to occur during a cutting procedure. This could possibly result in the revolving cutting tool 44 damaging an otherwise healthy tooth surface. Also, assuming all other contributing factors are equal, the electric handpiece 40, which is three times the weight of an air handpiece 30, will be more likely to slip in the dentist's grip due to the increased weight.

Another disadvantage of current designs relates to serviceability. Air and electric handpieces have spindle drive components located in the head area that will need to be serviced at some point in time. This includes the two spindle shaft bearings and the spindle tool chucking assembly. Air handpieces generally have a removable threaded end cap located on the top of the handpiece head. Removal of this end cap allows the spindle chucking assembly, generally referred to as a "turbine cartridge" for air handpieces, to be easily removed for servicing. Replacement of the turbine cartridge of an air handpiece takes only two minutes or less and can be easily performed in the dental office. If an air handpiece turbine cartridge suddenly stops rotating in the middle of a procedure, it is practical to replace the cartridge while the patient remains in the dental chair.

Currently marketed electric handpieces employ spindle chucking assemblies that cannot be serviced by simply removing a top end cap. The complete spindle assembly cannot be removed because the motor gear on the motor shaft traps the lower spindle bearing. Cutting tool speeds in the vicinity of 220,000 RPM are required for a significant portion of dental procedures. Because electric motors having speeds greater than 110,000 RPM are not currently available, a 2:1 ratio speed increasing gear set is required to obtain cutting tool speeds near 220,000 RPM. Air and electric dental handpieces use miniature spindle bearings to keep the head diameter of the handpiece within acceptable limits. The bearings have limited life and will need to be replaced periodically.

The spindle chucking assembly of currently marketed electric powered handpieces includes a spindle gear which is driven by a gear located on the electric motor shaft. The spindle gear is mounted on the collet shaft of the spindle chucking assembly and is located between the two spindle bearings. In order for the lower spindle bearing to clear the motor gear on removal (as part of the spindle chucking assembly), the spindle gear would need to have an outside diameter greater than the lower spindle bearing. This would require the motor gear, because of the 2:1 drive ratio, to have an outside diameter approximately twice that of the spindle bearings. A motor gear having a diameter approximately twice the diameter of the spindle bearings is not practical because the head and lower handle portion diameters adjacent to the head would need to be enlarged significantly to clear the motor gear. The resulting lower handle portion diameter would be too large for the dentist to comfortably grip.

Currently marketed electric handpieces require the entire motor assembly and all jackshaft assemblies be removed in order to remove the lower spindle bearing. Unfortunately, removal of the electric motor assembly and associated jackshaft assemblies cannot be initiated until other electric handpiece components are removed. The other electric handpiece components include the upper and lower handle portions, the four fluid carrying tubes and the fiber optic light pipe. Additionally, electrical contacts and associated lead wires to the motor windings would also have to be removed. This is a very involved procedure which is impractical to perform in the dental office. As a result, currently marketed electric powered handpieces typically need to be sent to a dealer or manufacturer for servicing. Sending an electric handpiece to a dealer or manufacturer for servicing is a major problem because it requires the dentist to spend additional money to purchase a spare electric handpiece for use whenever his original electric handpiece needs to be serviced.

Furthermore, current air and electric handpieces typically use multiple nozzles to deliver an air and water spray mixture to cool the cutting tool and tooth as well as to wash away cutting debris. A multiple nozzle spray configuration is described in U.S. Pat. No. 3,199,196 to Lieb et al. The nozzles are equally spaced around the lower head periphery of the handpiece and are designed to produce spray jets from multiple directions. A multiple spray nozzle arrangement of at least three nozzles is advantageous because frequently a portion of a tooth will deflect one or two of the multiple spray jets away from the cutting tool work zone on a tooth. A minimum of three spray nozzles insures that there will always be at least one undeflected spray jet to cool the cutting area. Thus cutter tool and tooth overheating will be avoided. Single jet spray handpieces will need additional spray provided by a dental syringe in cases where a portion of a tooth deflects the spray jet. Although employment of a syringe to provide additional air and water spray is sufficient to keep the cutting zone cool, it is undesirable in that it adds yet another tool to the operating zone in the patient's oral cavity.

Multiple spray nozzle configurations generally involve the use of two circular distribution chambers for air and water. Each chamber is supplied air or water via a single tube inlet. Unfortunately, over time and particularly with dental operatories having relatively hard supply water, scale deposits will grow in the water spray lines. At some point, the resulting spray will become inadequate and the flow restriction will need to be removed. Approximately 70% of the water flow path in typical multiple spray nozzle configurations can be cleaned with a small diameter wire or a miniature drill bit mounted in a pin vise. The remaining 30% of the situations that cannot be cleaned will require the handpiece be sent back to the manufacturer. The manufacturer will then have to machine away a portion of the spray chamber wall to gain access to the restriction. Following removal of the restriction a new chamber wall will then need to be pressed into place. Again, sending of the handpiece to a dealer or manufacturer for servicing is not desirable.

Another reason that discourages dentists from purchasing currently marketed electric powered handpieces is associated with an optional fiber optic illumination provision and an optional swivel connection. A significant percentage of air handpieces purchased by dentists incorporate either or both of these options. Fiber optic illumination is used to provide additional lighting to the cutting tool work area. A swivel connection between the handpiece and delivery hose substantially decreases the reactionary drag torque caused by the delivery hose.

Depending on the area of a tooth to be prepared and surrounding clearances, it may be necessary to rotate the handpiece about the long handle axis to position the cutting tool at an optimum angle. If a swivel connector is not employed, the section of the delivery hose immediately attached to the rear handle area of the handpiece will need to rotate through the same angle as the handpiece. Because the opposite end of the delivery hose is attached to the dental delivery system, the opposite end does not rotate. Therefore, whenever the handpiece is rotated as described above, the delivery hose is subjected to a net "twisting" displacement. A twisting torque must be supplied to the handpiece end of delivery hose to cause the net twisting.

The amount of reactionary drag torque necessary to rotate the handpiece end of the delivery hose is directly proportional to the relative amount of twisting displacement of the delivery hose caused by the handpiece rotation. A torque must be supplied along the handpiece handle to counteract the delivery hose drag torque. The torque is supplied by the dentist's three finger grip at the lower handle portion of the handpiece. Application of the torque requires the dentist to supply a circumferential force at each of the three fingers involved in the grip. Also, a radially inward gripping force must be supplied by the three fingers to insure the handpiece handle does not rotationally slip relative to the dentist's hand. The circumferential and radial forces required to counteract the delivery hose torque are in addition to the gripping forces necessary to support the weight of the handpiece described earlier.

A dual fiber optic and swivel option is available with most air handpieces. In such dual option air handpieces, the fiber optic light pipe is typically placed at the central axis of the swivel connector in order to keep the design as simple as possible. However, currently available electric handpieces which have swivel connections typically locate the motor shaft, or one of the two jackshafts, at the central axis of the swivel connector to keep the mechanical design as simple as possible. As such, it is not possible to have the rotating shaft and the fiber optic light pipe sharing the same central axis.

An additional factor responsible for the relatively low sales of current electric powered handpieces is price. Current electric handpieces cost more than air handpieces because of the need to provide electronic controls and the costs of the electric motor and the two jackshaft subassemblies.

Despite the control disadvantages of air powered handpieces and the significant control advantages of electric powered handpieces, the fact that only approximately 15% of handpieces sold in the United States are electric, indicates that dentists consider these disadvantages of prior art electric handpieces to be very significant.

SUMMARY OF THE INVENTION

In one aspect, the present invention provides an electric dental handpiece including a head engaging a handle and configured to rotatably support a tool. The handle includes a lower handle portion and an upper handle portion with the lower handle portion engaging the head and the upper handle portion having an attachment area configured for attachment to a power supply. An electric motor is positioned within the lower handle portion and is configured to rotate the tool.

In another aspect, the present invention provides an electric dental handpiece including a head configured to rotatably support a tool and a handle defining a lower handle portion and an upper handle portion joined proximate to a rear gripping area of the handle with the lower handle portion engaging the head and the upper handle portion having an attachment area configured for attachment to a power supply. A forward gripping area of the handle is defined proximate to the head. An electric motor configured to rotate the tool is positioned with a majority thereof within the lower handle portion such that a center of gravity of the handpiece is within the lower handle portion.

BRIEF DESCRIPTION OF THE DRAWINGS

FIG. 1 is a schematic force distribution diagram of a typical air powered dental handpiece when gripped by a simulated dentist's hand.

FIG. 2 is a schematic force distribution diagram of a currently available electric motor powered dental handpiece when gripped by a simulated dentist's hand.

FIG. 3 is an exploded view, in partial section, of an electric handpiece according to an exemplary embodiment of the present invention.

DETAILED DESCRIPTION OF THE INVENTION

Figure 4:
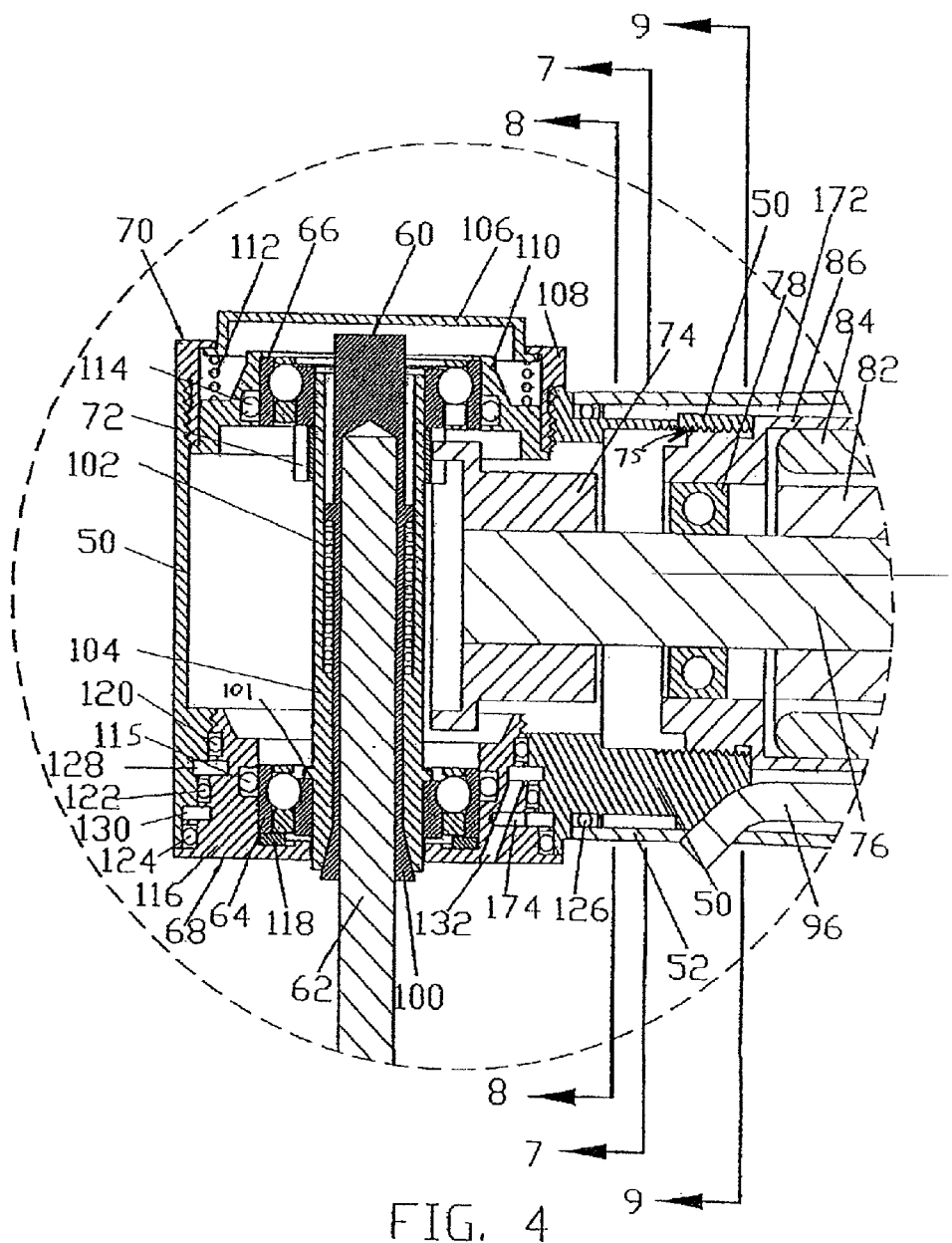
FIG. 4 is an enlarged sectional view illustrating the interface between the handpiece head and electric motor of the electric handpiece of FIG. 3.

Although the invention is illustrated and described herein with reference to specific embodiments, the invention is not intended to be limited to the details shown. Rather, various modifications may be made in the details within the scope and range of equivalents of the claims and without departing from the invention.

In at least one embodiment, the motor control method employs a sensor or multiple sensors to determine motor shaft rotational position. However, alternative motor controlling methods are available that eliminate the need to employ sensors within the motor. For example, in some embodiments it is not necessary to monitor the motor shaft rotational position and the sensors may be eliminated, thereby simplifying the motor design and reducing wiring requirements.

Some alternative methods involve the use of additional circuitry in the motor controlling device and are based on the sequential activation of individual motor winding coils. For example, when three motor windings are used to power a motor, there will always be two winding coils receiving electrical power at any given time. The additional circuitry required is designed to sense the back EMF of the winding coil that is not powered. The back EMF is generated by the physical motion of the magnetically reactive material relative to the fixed position of the winding that is momentarily not powered. The circuitry senses the temporal characteristics of the back EMF and delivers this data to the microprocessor involved in motor controlling. The microprocessor analyzes the data, calculates an actual instantaneous motor shaft speed and compares it to the desired rotational speed in its memory. If a difference occurs between the desired and actual speeds, the microprocessor adjusts the voltage level and timing of the waveforms to be sent to the motor windings.

There are advantages and disadvantages to the various methods of motor control. The current invention is not limited by the method of motor control, and may employ any of various techniques, including, but not limited to, the two described above. For the sake of discussion and description simplicity, the motor control method which employs one or more sensors is described with respect to the first embodiment of the invention. Furthermore, there are variations of the number and types of sensors involved to determine the motor shaft rotational position. Some methods use a single sensor while other may use two or more sensors. For the sake of discussion and description simplicity, a method which uses a single sensor has been described. This description is not meant to imply this method is superior, nor required.

Referring to FIG. 3, an electric handpiece assembly 48 that is a first exemplary embodiment of the present invention is shown. The electric handpiece assembly 48 includes an electric motor assembly 164 configured to drive a spindle chucking assembly 60. The spindle chucking assembly 60 is configured to grip a desired tool 62, the illustrated tool 62 being a cutting tool. The handpiece assembly 48 generally comprises a head 50, a handle 49 comprising a lower handle portion 52 and an upper handle portion 54, an upper end cap assembly 70, a lower end cap assembly 68, a motor assembly 164 and a spindle chucking assembly 60. The upper handle portion 54 is attached to lower handle portion 52 and the interface is sealed by handle joint O-rings 98. As mentioned previously, the actual handle construction can be significantly different than that illustrated without affecting the scope and intent of the invention.

The handpiece assembly 48 is connected to a multiple line delivery hose 58 by means of a delivery hose adapter 56. The interface between the handpiece assembly 48 and the delivery hose adapter 56 includes a sealing provision 166 for each of the fluid lines in the delivery hose 58. The physical connection between the handpiece assembly 48 and the delivery hose adapter 56 can be a threaded connection, a swivel connection, or any other desired connection. The connection preferably incorporates a locking device (not shown) to prevent accidental separation of the handpiece 48 from the delivery hose adapter 56. The delivery hose 58 extends to the dental delivery system 178 (see FIG. 13) which supplies air, water and electric power to the handpiece assembly 48.

Figure 15:
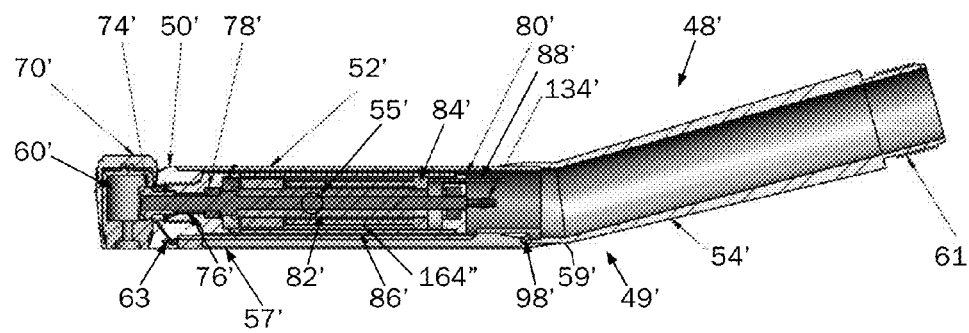
FIG. 15 is a side elevation view, in cross-section, of an electric handpiece according to another exemplary embodiment of the present invention.
Figure 16:
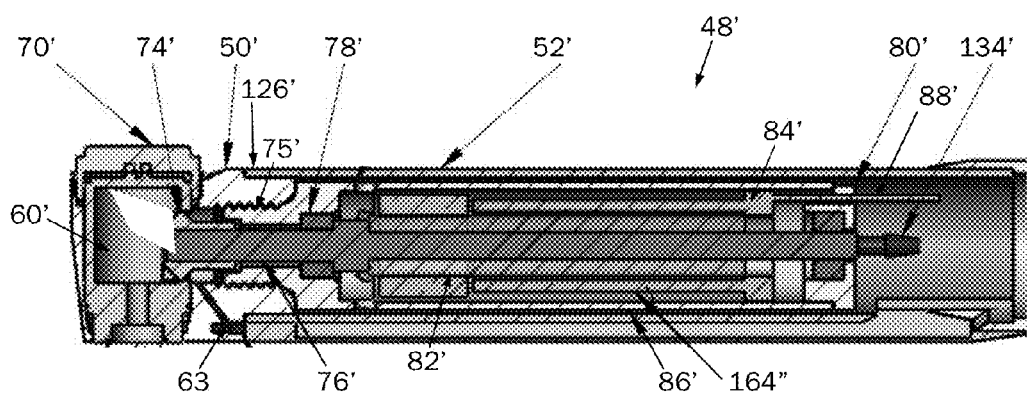
FIG. 16 is an expanded view of the lower handle portion of the electric handpiece of FIG. 15.
Figure 17:
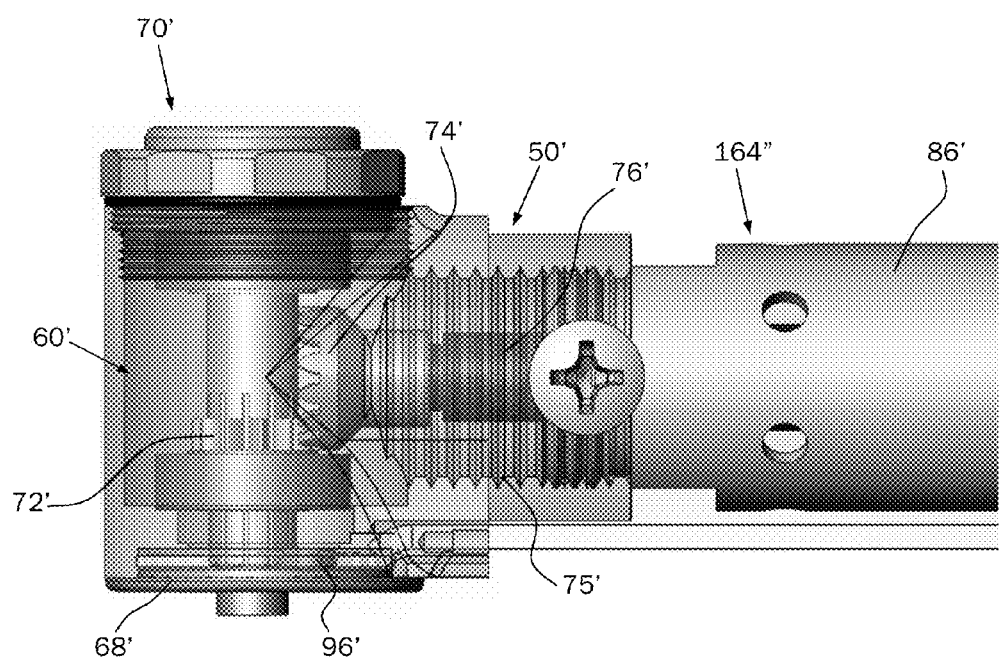
FIG. 17 is an expanded view of the head area of the electric handpiece of FIG. 15 with the handle body removed and the head body shown translucently.
Figure 18:
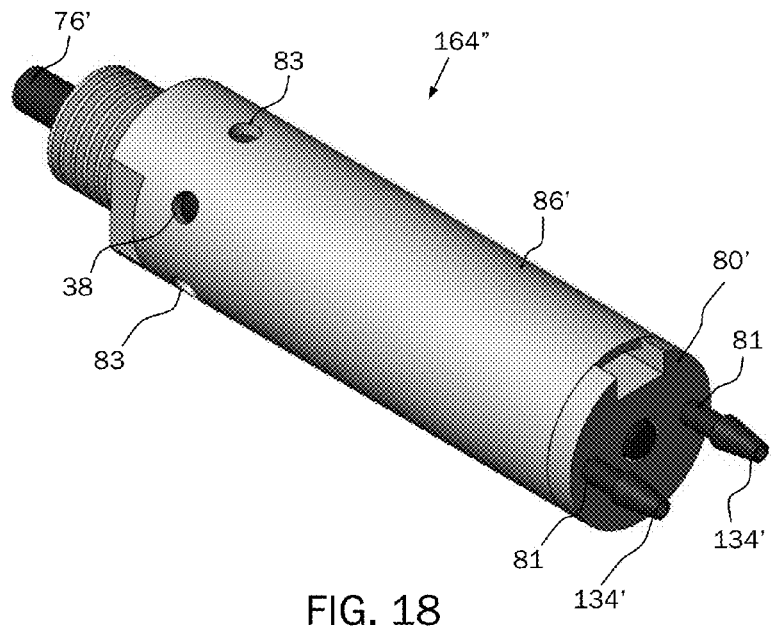
FIG. 18 is an isometric view of the motor assembly of the electric handpiece of FIG. 15.
Figure 19:
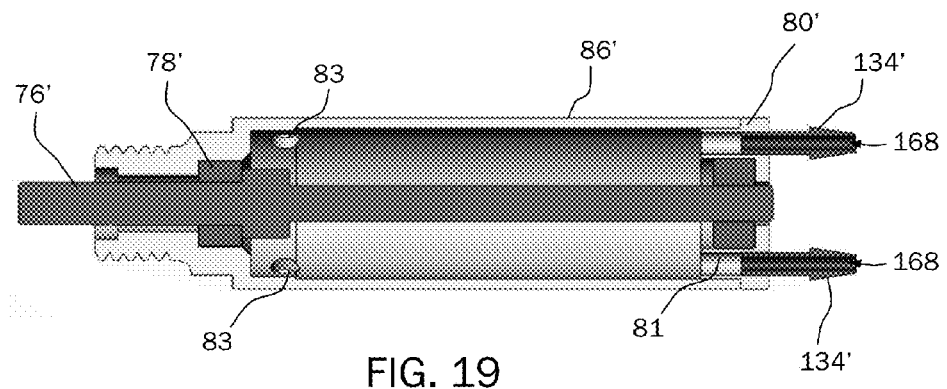
FIG. 19 is a cross-sectional view along the line 19-19 of FIG. 18.

Referring to FIGS. 15 and 16, an electric handpiece assembly 48' that is another exemplary embodiment of the present invention is shown. The electric handpiece assembly 48' is similar to the previous embodiment and includes an electric motor assembly 164" configured to drive a spindle chucking assembly 60'. The spindle chucking assembly 60' is configured to grip a desired tool (not shown). The handpiece assembly 48' generally comprises a head 50', a handle 49' comprising a lower handle portion 52' and an upper handle portion 54', an upper end cap assembly 70', a lower end cap assembly 68', a motor assembly 164" and a spindle chucking assembly 60'. The upper handle portion 54' is attached to lower handle portion 52' and the interface is sealed by handle joint O-rings 98'. As mentioned previously, the actual handle construction can be significantly different than that illustrated without affecting the scope and intent of the invention.

The handpiece assembly 48' is connected to a multiple line delivery hose 58 by means of a delivery hose adapter (not shown). The interface between the handpiece assembly 48' and the delivery hose adapter includes a sealing provision for each of the fluid lines in the delivery hose 58. The physical connection between the handpiece assembly 48' and the delivery hose adapter can be a threaded connection 61, a swivel connection, or any other desired connection. The connection 61 preferably incorporates a locking device (not shown) to prevent accidental separation of the handpiece 48' from the delivery hose adapter. The delivery hose 58 extends to the dental delivery system 178 (see FIG. 13) which supplies air, water, electric power and lubrication oil to the handpiece assembly 48'. The lubricant oil is supplied via a lubricant supply line 63 extending through the handle 49' and is configured to lubricate the head assembly. Cooling air may also be passed through the lubricant supply line 63, in alternating fashion or as a mixture with the lubrication oil, to assist in cooling the gears and the head.

Figure 5:
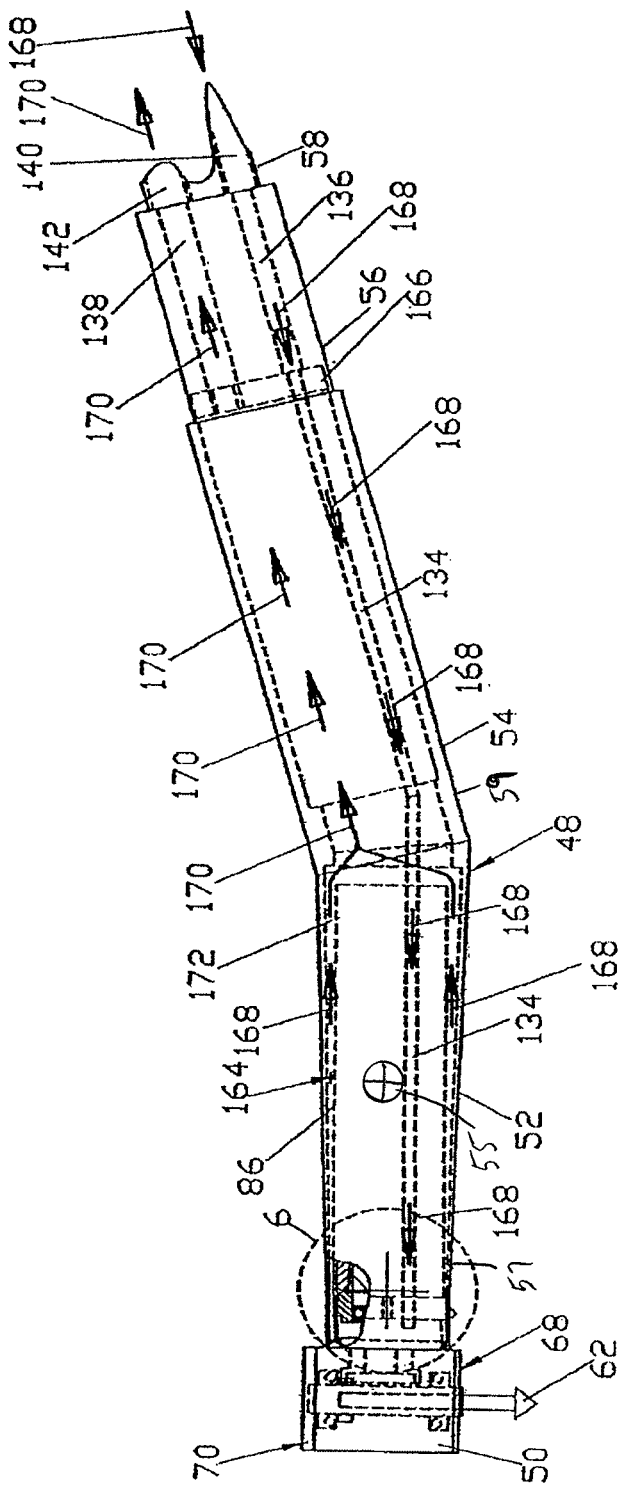
FIG. 5 is a side elevation view of the electric handpiece of FIG. 3 with the motor cooling air paths illustrated in phantom.

The electric motor assembly 164, 164" includes a motor housing 86, 86' which is primarily positioned in the lower handle portion 52, 52' and houses the majority of motor components. With reference to FIGS. 3, 5 and 15, in each embodiment the motor assembly 164, 164" is positioned within the lower handle portion 52, 52' and the upper handle portion 54, 54' remains substantially hollow except for the passage of wiring, tubing and the like. As a result, the center of gravity 55, 55' of the handpiece 48, 48' is within the lower handle portion 52, 52' and positioned between the front gripping area 57, 57' and the rear gripping area 59, 59'.

Motor windings 84, 84' are attached to the inside surface of the motor housing 86, 86'. A motor shaft 76, 76' is supported by a motor front bearing 78, 78' and a motor rear bearing 80, 80'. The bearings 78, 78', 80, 80' may be manufactured from a ceramic material to reduce the need for lubrication. A magnetically reactive material ("MRM") 82, 82' which is either attracted to or repelled by the motor windings 84, 84' is attached to motor shaft 76, 76'. In a preferred embodiment, the MRM 82, 82' is a rare earth metal. Electrical power is supplied to the motor windings 84, 84' by motor winding leads 88, 88'. While the invention is described herein as having three windings, in practice, the number of windings can be fewer than three or more than three. Also, various types of commutation can be employed, for example, but not limited to, brush type, brushless with sensors and brushless without sensors.

In the handpiece 48, the rotational position of the motor shaft 76 is determined by a shaft position sensor 90. The shaft position sensor 90 detects a shaft position reference device 160 which is attached to the motor shaft 76. The shaft position sensor 90 is attached to a shaft position sensor support 92 which in turn is attached to the inside of the motor housing 86. Electrical power to the shaft position sensor 90 is provided by shaft position sensor leads 94 which also serve as the electrical path for output signals from the shaft position sensor 90. A shaft position reference counterweight 162 is attached to the motor shaft 76 and is provided to counterbalance the weight of the shaft position reference device 160.

A motor gear 74, 74' is attached to the external portion of the motor shaft 76, 76' and is configured to drive a spindle gear 72, 72', as described hereinafter. The motor assembly 164, 164' is illustrated and described as having a motor shaft 76, 76' and a motor gear 74, 74' attached directly thereto. The number of teeth on the motor gear 74, 74' and the spindle gear 72, 72' can be varied to a limited extent to cause the cutting tool 62 to rotate faster or slower than the motor shaft 76, 76'. Assuming the maximum speed of motor shaft 76, 76' is 110,000 RPM, the limiting speed increasing ratio that can be achieved by the motor gear 74, 74' and the spindle gear 72, 72' is approximately a 2:1 increasing ratio, which results in a cutting tool 62 maximum speed of 220,000 RPM. The limiting speed reduction ratio that can be achieved by the motor gear 74, 74' and the spindle gear 72, 72' is approximately a 2:1 reduction ratio, which would result in a cutting tool minimum speed of 55,000 RPM.

Figure 4A:
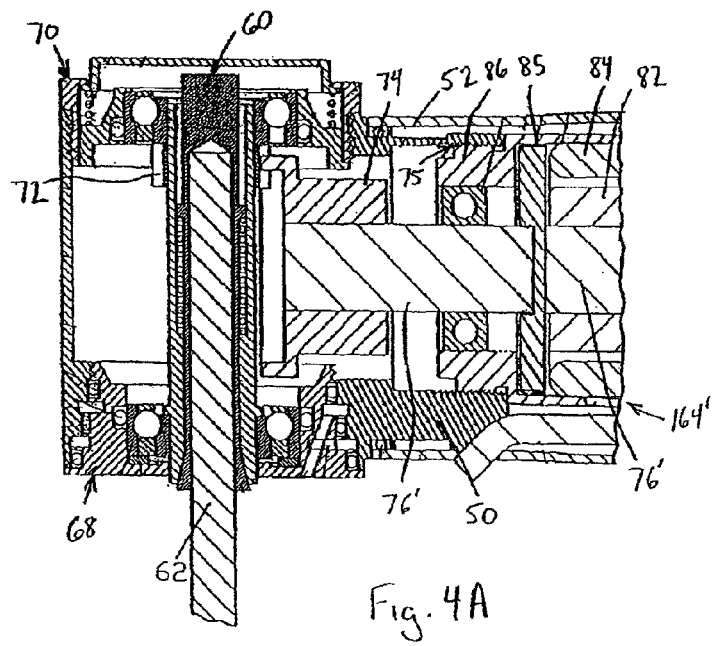
FIGS. 4A and 4B are views similar to FIG. 4, illustrating alternative exemplary embodiments of the present invention.
Figure 4B:
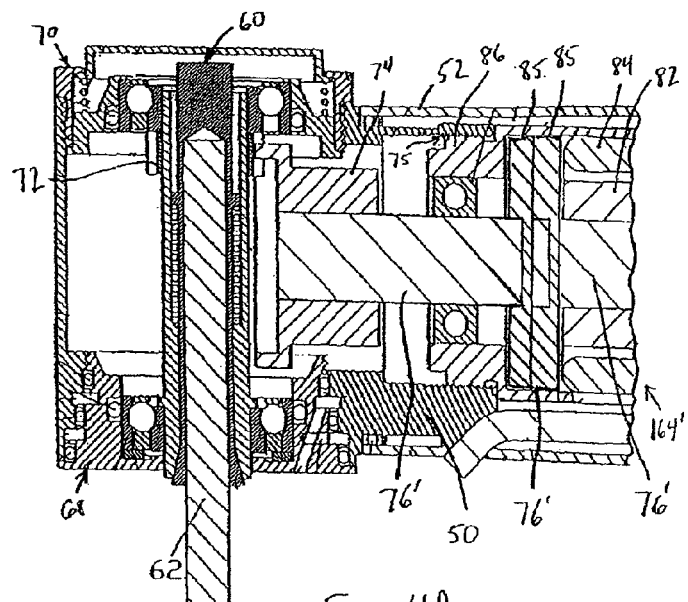

Some dental procedures, such as dental prophylaxis, require very low cutting tool 62 speeds on the order of 2,000 RPM or less. In order to achieve very low tool 62 speeds, it is necessary to use what is referred to as a "gearmotor". The gearmotor 164' as illustrated in FIGS. 4A and 4B is comprised of a motor assembly similar to motor assembly 164, 164", but further includes one or more sets of reducing gears along the motor shaft 76 configured to produce significantly lower output shaft speeds. The preferred reducing gears are planetary gear reduction sets 85. They have a distinct advantage in that the gear reducing hardware can be made to fit into a housing which is the same diameter as the driving motor housing 86. While planetary gear sets are preferred, other reducing gear configurations may be utilized.

Referring to FIGS. 4A and 4B, the motor assembly 164' is substantially the same as the motor assembly 164, 164", but includes a segmented motor shaft 76' with one or more planetary gear sets 85 adjoining the shaft sections 76' and producing the desired gear reduction. The motor assembly 164' has exactly the same threaded mounting configuration as the direct drive motor assembly 164, 164". The output shaft 76' diameter and shaft length of the motor assembly 164' also matches those of the direct drive motor assembly 164, 164". The motor gear 74 is mounted to the output shaft 76' and drives the spindle gear 72 in the same manner as the direct drive motor assembly 164, 164" illustrated in FIG. 4. The only physical difference between the gear reducing motor assemblies of FIGS. 4A and 4B and the direct drive motor assembly 164, 164" of FIG. 4 is that the housing 86 length of the motor assemblies of FIGS. 4A and 4B is slightly longer. The incremental length increase is directly proportional to the number of planetary gear sets 85 employed. The motor assembly 164' with a single planetary gear set 85 illustrated in FIG. 4A has about a 5:1 speed reduction factor. The motor assembly 164' with two planetary gear sets 85 illustrated in FIG. 4B has about a 25:1 speed reduction factor and has a housing length that is slightly longer than the single stage or the direct drive motor housing 86.

The various descriptions which follow as well as those which have preceded, contain numerous references to a direct drive motor assembly 164, 164". With very few exceptions, the references to the direct drive motor assembly 164, 164" incorporate the assemblies of FIGS. 4, 4A, 4B and 15 or assemblies with more than two gear reducing sets. Therefore the word "motor" in all of the text of this document, refers to both the "direct drive motor" and gear reduction motor variations. In cases where the text applies only to the gear reduction motor variation, the word "gearmotor" is used.

The direct interconnection between the motor gear 74, 74' on the motor shaft 76, 76' with the spindle gear 72, 72' has allowed the elimination of all two jackshaft assemblies found in prior art electric dental handpieces. Each of these prior art jackshaft assemblies contains several rotating parts including bevel gears and support bearings. Elimination of all jackshaft subassemblies results in a cost savings, increases the reliability of electric handpiece 48, 48', has lowered the overall handpiece noise level, and has moved the center of gravity 55, 55' of the handpiece 48, 48' forward.

In designing an electric handpiece 48, 48' with the motor assembly 164, 164" primarily positioned in the lower handle portion 52, 52', it was recognized that a smaller motor was desirable, but the motor still required sufficient operational speed and torque. It was further recognized that while electric motor manufacturers publish electric motor specifications which list speed and torque values for the motors they offer, it is generally unknown that published torque ratings are significantly less than the maximum amounts motors are actually capable of delivering. The published torque values are based on torques that can be continuously generated without damaging motor windings due to excessive temperature. When a manufacturer specifies a torque limit, it is typically assumed that the motor is to be running at a slightly elevated room temperature without any externally applied cooling.

It was recognized that a smaller motor assembly 164, 164" can be utilized and deliver torques significantly greater than its published values by providing external cooling to the motor windings to prevent excessive temperatures. The electric motor assembly 164, 164" preferably includes copper windings 84, 84' capable of safe operation at temperature up to 300 degrees F. However, as the motor winding temperature increases, the resistance of the copper winding 84, 84' also increases. As a result, a larger percentage of the supplied electrical power would be lost to heat in the motor windings. Because less of the total supplied power will be available to produce torque, the motor assembly 164, 164" would have a noticeable drop in torque if the winding temperature is allowed to rise unabated. Furthermore, excessive heat transfer between the motor housing 86, 86' and the close lower handle portion 52, 52' would be undesirable.

The potential heat problems are avoided by providing a motor cooling assembly. In the illustrated embodiments, the motor cooling assembly diverts compressed air, which would have been originally supplied to power the turbine in an air handpiece, to the area between the external motor housing 86, 86' surface and the internal surface of the lower handle portion 52, 52'. This technique significantly limits the lower handle portion 52, 52' and motor housing 86, 86' temperature rises. The motor housing 86, 86' acts as an efficient heat sink, and because of the proximity of the motor windings 84, 84' to the motor housing 86, 86', the winding temperature is significantly lowered.

Figure 13:
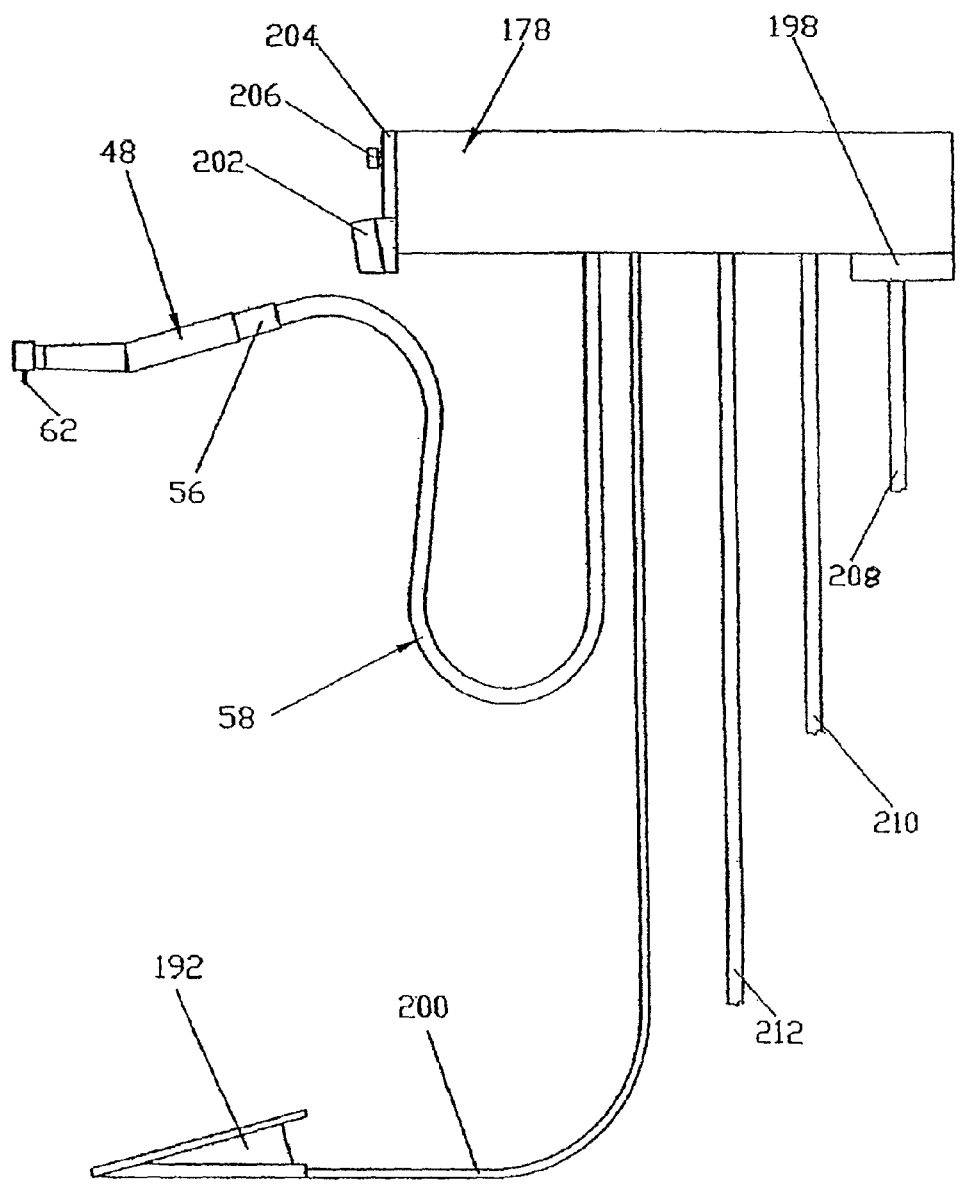
FIG. 13 is a schematic drawing illustrating the physical relationship of the electric handpiece and major supportive equipment.

An exemplary motor cooling assembly is illustrated in FIGS. 5-9 and 13. Referring to FIGS. 5 and 13, motor cooling air inlet flow 168 is supplied from the dental delivery system 178 to a cooling air inlet line 140 in the delivery hose 58. Cooling air flow 168 then passes through the cooling air inlet line 136 of the delivery hose adapter 56. Cooling air flow 168 then passes through the sealing provision 166 and is then directed to one or more cooling air tubes 134.

Figure 6:
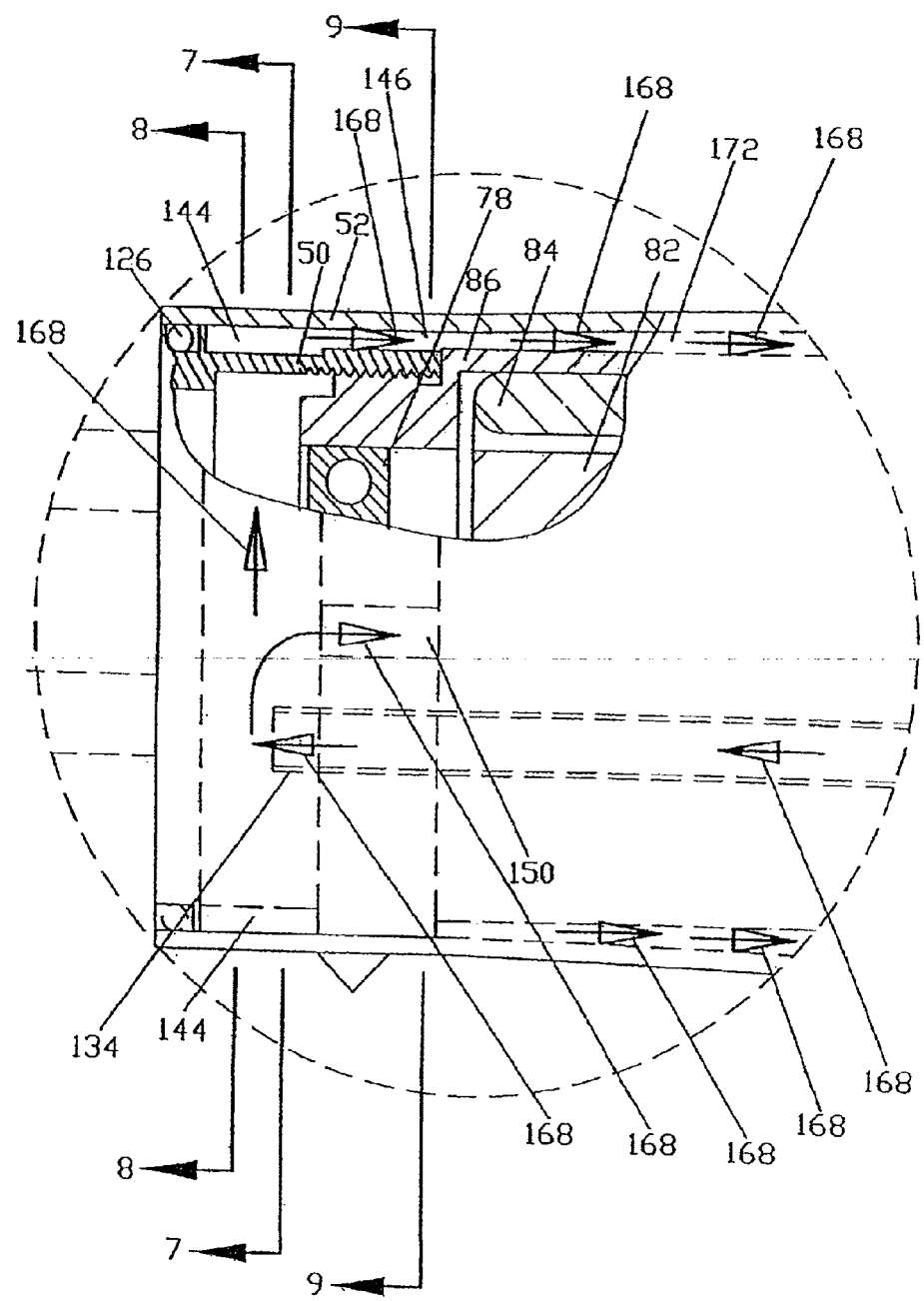
FIG. 6 is an enlarged, partial sectional view of a portion of the lower handle portion.
Figure 7:
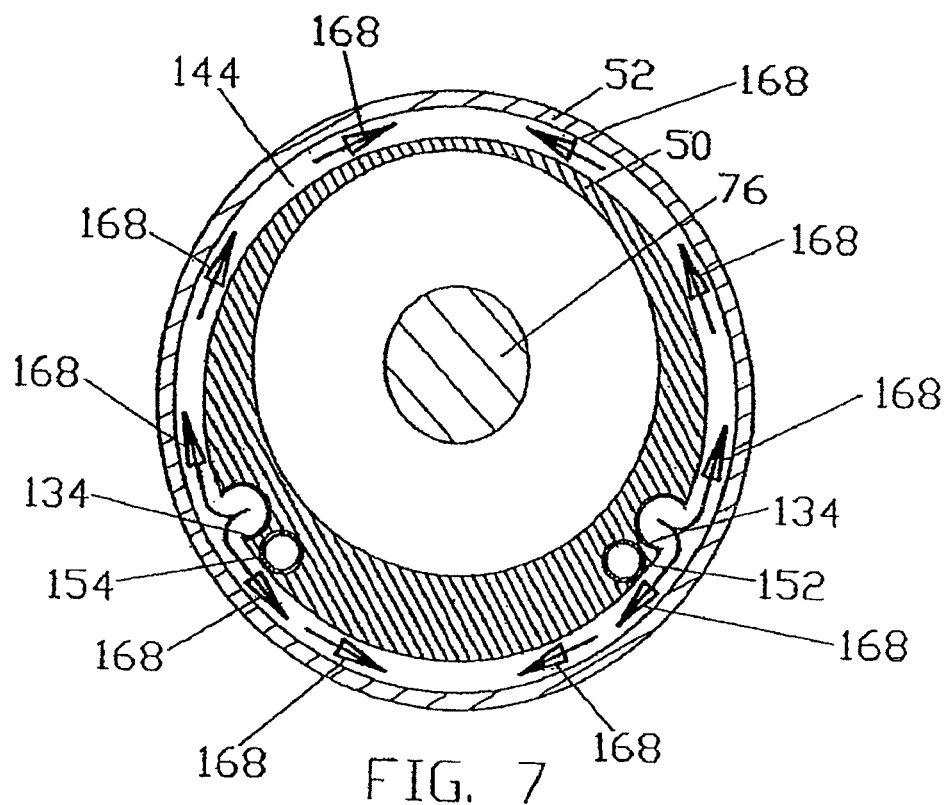
FIG. 7 is a cross-sectional view along the line 7-7 in FIGS. 3 and 6.
Figure 8:
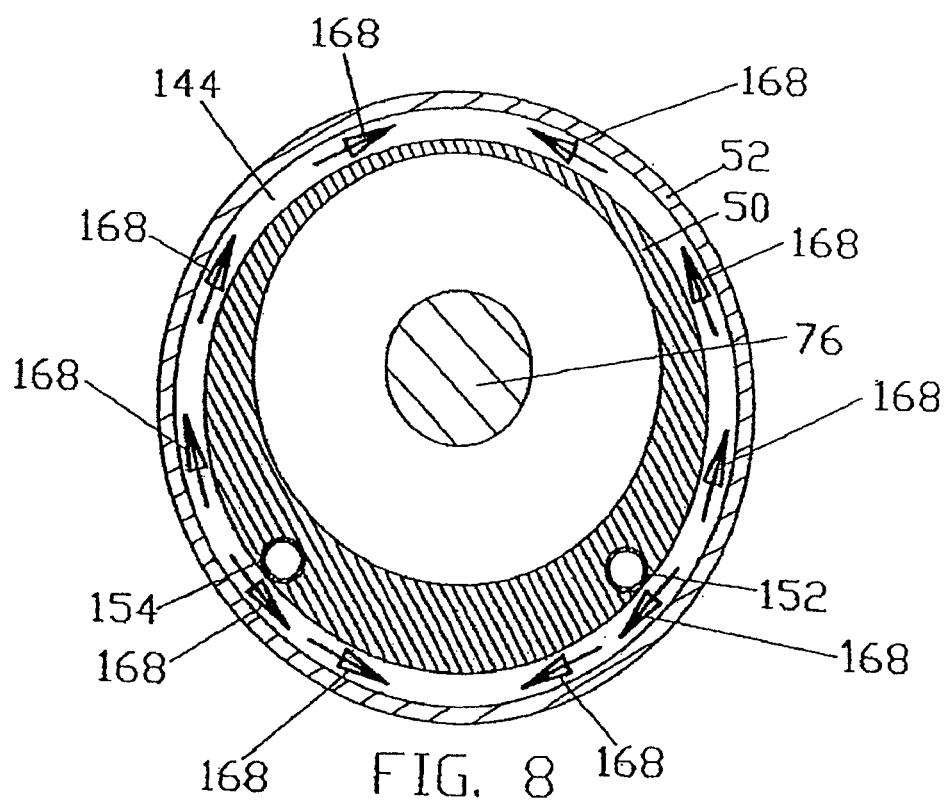
FIG. 8 is a cross-sectional view along the line 8-8 in FIGS. 3 and 6.
Figure 9:
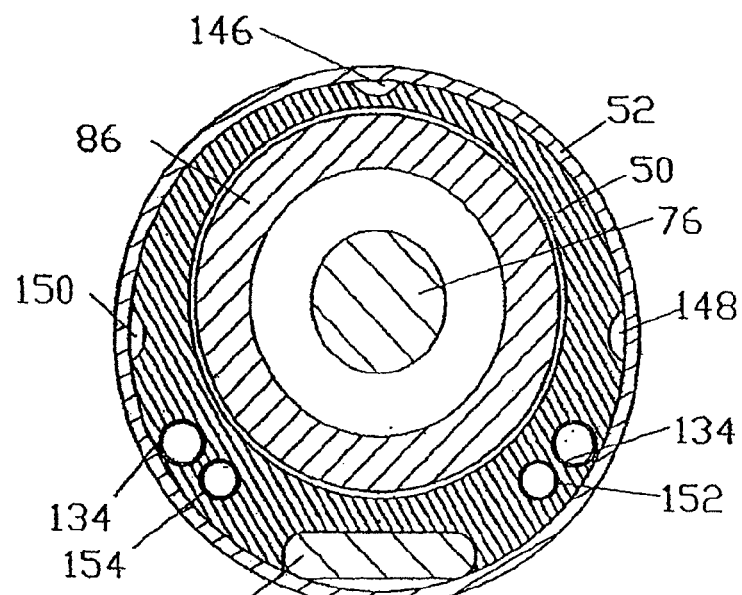
FIG. 9 is a cross-sectional view along the line 9-9 in FIGS. 3 and 6.

Referring to FIG. 6, cooling air tubes 134 are attached to the head 50. Cooling air flow 168, after passing through the cooling air tube 134, is directed into the motor cooling air distribution chamber 144. FIG. 7 is a sectional view of the handpiece 48 in a direction perpendicular to the longitudinal axis of the handpiece 48, as indicated by the section lines in FIG. 6. FIG. 7 shows how cooling air flow 168 transfers from an axial flow in cooling air tube 134 into a circumferential flow in the motor cooling chamber 144. The inside surface of lower handle portion 52 is the outer wall of the motor cooling air distribution chamber 144. FIG. 8 is another section similar to FIG. 7, but is taken at an axial location closer to the head 50, slightly forward of the end of the cooling air tube 134. After cooling air flow 168 distributes itself uniformly in a circumferential direction in the motor cooling chamber 144, it is forced to now travel in an axial direction away from the head 50. Referring to FIG. 9, cooling air flow 168 is now directed into three nozzles, namely motor cooling nozzle-top 146, motor cooling nozzle-right 148 and motor cooling nozzle-left 150. The nozzles 146, 148 and 150 act to uniformly distribute cooling air flow 168 into the motor-lower handle portion annular pathway 172 as illustrated in FIG. 6. Referring back to FIG. 5, cooling air flow 168 now flows in an axial direction away from the head 50. Cooling air flow 168 will continue flowing in the motor-lower handle portion annular pathway 172 until it reaches the end of the motor housing 86.

Cooling air flow 168 will have risen in temperature as heat is transferred from the motor housing 86. The flow will now be referred to as "motor cooling air exhaust flow 170". Motor cooling air exhaust flow 170 now moves axially away from the head 50 into the internal cavity of lower handle portion 52 and then into the internal cavity of upper handle portion 54. The exhaust air flow 170 then passes through the sealing provision 166 and into the exhaust air outlet line 138 of delivery the hose adapter 56. Exhaust air flow 170 then passes through the exhaust air outlet line 142 of the delivery hose 58 and is then exhausted into the dental delivery system 178.

Although using compressed air to cool the motor housing 86 and lower handle portion 52 of the electric handpiece 48 is very effective when the handpiece 48 is in use, the external handle surface temperature has been found to rise 20 to 40 degrees F. after handpiece use is terminated. It has been determined that the temperature rise of the windings when cooled by compressed air, can range from 30 to 100 degrees F. above ambient during handpiece use. When handpiece use is discontinued, electric current to the motor windings 84 and cooling air are simultaneously removed. However, at the moment cooling air is removed, the windings 84 will have heat energy stored at temperatures of up to 100 degrees F. above ambient. Therefore, the windings 84 are able to transfer heat to the lower handle portion 52 for several minutes. This can cause a momentary lower handle portion 52 temperature rise of 20 to 40 degrees F.

To prevent this temperature rise in the lower handle portion 52 after handpiece use is terminated, cooling air flow 168 is provided for a period after use of the handpiece 48 is terminated. Such additional cooling period may be for a fixed period or some other calculated period, for example, a timed period proportional to the time of use of the handpiece 48. Alternatively, a temperature measuring device may be used as a means to control the duration of the additional cooling cycle such that cooling air is provided until the windings 84 are below a desired temperature.

In the preferred embodiment, a logic circuit is provided to control the additional cooling following handpiece use. This circuit is designed to measure the resistance change of the copper windings that occurs at temperatures above ambient. Because the electrical resistivity of copper has a high temperature coefficient, there is a significant increase in the resistance of motor windings 84 above the ambient value due to the temperature rise occurring in motor windings 84. The temperature rise in motor windings 84 is a normal event that occurs due to electrical current flowing through the resistance of motor windings 84. The temperature rise is not transmitted to the lower handle portion 52 during normal handpiece 48 use because the motor cooling air inlet flow 168 acts as a very efficient heat transfer medium. However the temperature of motor windings 84 at the moment handpiece 48 use is discontinued, is significantly higher than ambient. If motor cooling air inlet flow 168 is not provided, significant heat energy will flow from the motor windings 84, through motor housing 86 and to the lower handle portion 52, thereby increasing the external temperature of the lower handle portion 52.

Figure 14:
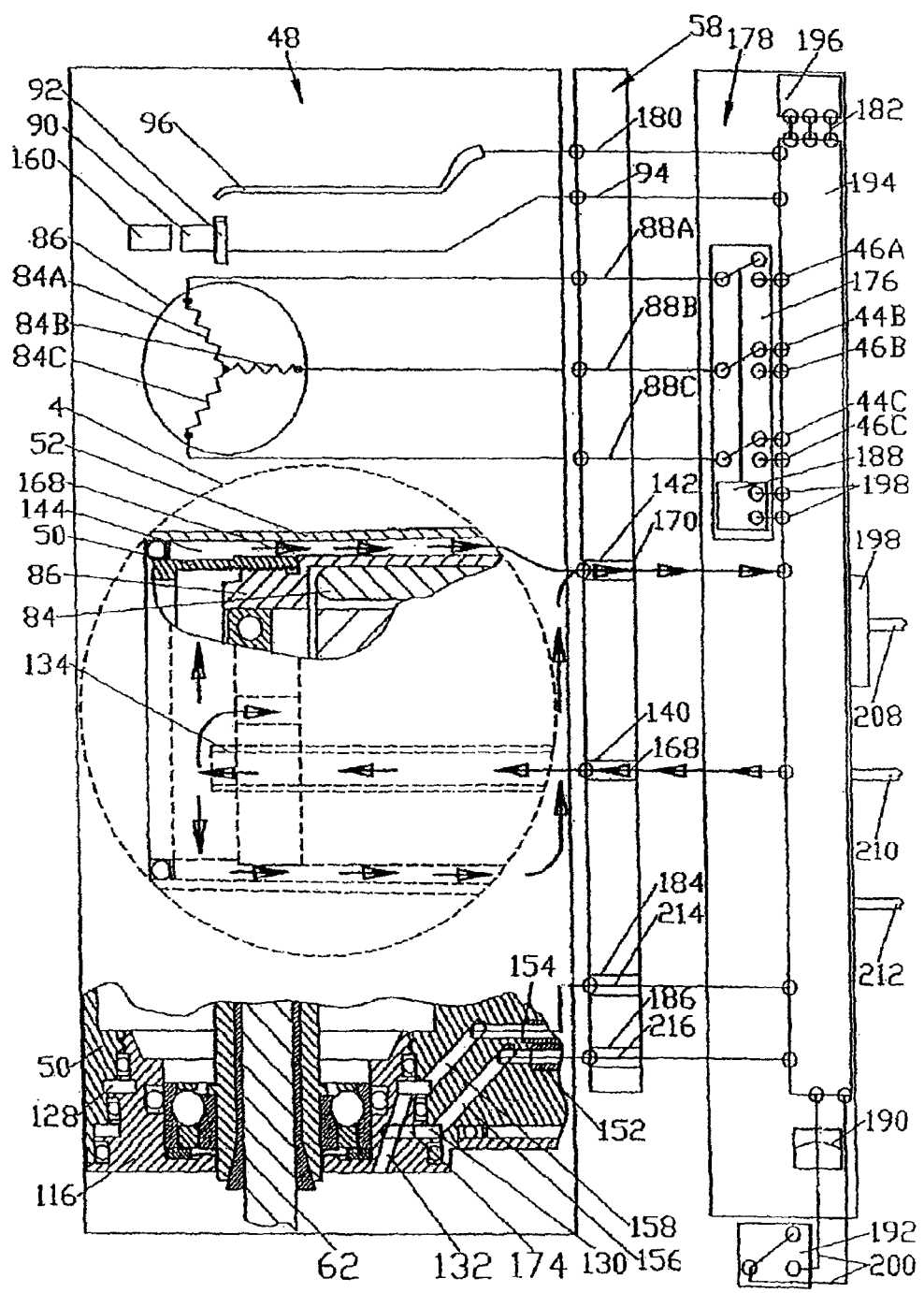
FIG. 14 is a schematic drawing illustrating the systematic relationship of the electric handpiece and major supportive equipment.

An electrical circuit that senses the resistance of motor windings 84 after handpiece 48 use is discontinued has been incorporated into the electrical circuitry of the controller 194. Referring to FIG. 14, an electrical relay 176 is used to switch two of the three of motor winding leads 88 from a normal "run motor" state to a "sense motor winding resistance" state. Motor winding leads 88B and 88C have been selected as the two motor winding leads that will be used to measure the combined resistance of motor windings 84B and 84C. The controller 194 uses resistance B terminal 44B and resistance C terminal 44C as input terminal points for measuring the combined resistance of motor winding 84B and motor winding 84C. Motor winding lead 84A, although not directly involved in the motor windings 84 resistance measurement technique, is intentionally switched to a disconnected or floating state. This has been done to prevent possible damage to the internal electronics of the controller 194 that are normally involved in powering motor windings 84A, 84B and 84C to cause the motor shaft 76 to rotate. The electrical relay 176 is configured to select the "sense motor winding resistance" state when the electrical relay coil 188 is not energized. FIG. 14 shows electrical relay 176 in the not energized state. The electrical relay coil 188 is energized via an electrical signal received, directly or indirectly, from the foot pedal cord 200 which is connected to the foot pedal 192. Energizing the electrical relay coil 188 causes the "run motor" state to be selected. Referring to FIG. 14, energizing relay coil 188, causes the following to occur:

A. Motor lead 88A is switched from a floating state to phase A terminal 46A on controller 194.

B. Motor lead 88B is switched from resistance B terminal 44B to phase B terminal 46B on controller 194.

C. Motor lead 88C is switched from resistance C terminal 44C to phase C terminal 46C on controller 194.

The sensed resistance of the motor windings 84 after handpiece 48 use is discontinued will be utilized by the controller to monitor the temperature of the motor windings 84. The system microprocessor 196, see FIG. 14, will continue to instruct controller 194 to supply motor cooling air inlet flow 168 and will continue to monitor the motor windings 84 resistance measuring signal. When the microprocessor 196 determines the motor windings 84 resistance has dropped to a level corresponding to an acceptable temperature, it will instruct the controller 194 to discontinue supplying motor cooling inlet air flow 168 to handpiece 48.

Referring to FIGS. 15-19, an alternative motor cooling assembly will be described. Similar to the previous embodiment, motor cooling air inlet flow 168 is supplied from the dental delivery system 178 to a cooling air inlet line 140 in the delivery hose 58. Cooling air flow 168 then passes through the cooling air inlet line 136 of the delivery hose adapter. Cooling air flow 168 then passes through the sealing provision and is then directed to one or more cooling air tubes 134'. In the present embodiment, the cooling air tubes 134' terminate in bores 81 in the rear bearing assembly 80'. Additional bores may be provided through the rear bearing assembly 80' to facilitate additional flow. As such, the cooling air flow 168 passes directly into the motor housing 86' wherein it passes across the MRM 82' and motor windings 84'. Air exhaust ports 83 are provided at the forward end of the motor housing 82' such that the cooling air flow 168 passes through the housing 86' and out of the ports 83. The air thereafter passes rearwardly between the motor housing 86' and the handle 49'. A control system as described above may be included to regulate the temperature.

Referring to FIGS. 3, 4, 16 and 17, the interface between the motor assembly 164, 164" and the head 50, 50' will be described. Lower handle portion 52, 52' is attached to head 50, 50' and head-lower handle portion O-ring 126, 126' seals the interface. In the present embodiment, screw threads 75, 75' extend between the motor assembly 164, 164" and the head 50, 50' to facilitate such interconnection. Upon connection of the head 50, 50' to the lower handle portion 52, 52', the motor gear 74, 74' mates with the spindle gear 72, 72'. The screw threads 75, 75' facilitate adjustment of the position of the motor gear 74, 74' relative to the spindle gear 72, 72'. The threads 75, 75' also allow the motor assembly 164, 164" to be easily removed if necessary. The spindle gear 72, 72' is attached to the spindle chucking assembly 60, 60' which grips the cutting tool 62.

Referring again to FIG. 4, the spindle chucking assembly 60 is comprised of a spindle shaft 104, a collet 100, a collet spring 102, an upper spindle bearing 66 and the spindle gear 72. The collet spring 102 pushes the collet 100 upward, causing the tapered lower section of the collet 100 to compress radially inward to grip the cutting tool 62. The spindle shaft 104 is pressed into the inner raceway of the upper bearing 66. The spindle shaft 104 has a sliding fit into the inner raceway of the lower spindle bearing 64. Axial movement of the lower bearing 64 is limited by a shoulder 101 on the spindle shaft 104. The spindle gear 72 is attached to the spindle shaft 104 and mates with and is driven by the motor gear 74.

The upper end cap assembly 70 is threaded into head 50 and includes a pushbutton 106, an upper threaded cap 108, an upper bearing cap 110, a pushbutton spring 112 and a bearing O-ring 114. The upper bearing cap 110 is pressed into the upper threaded cap 108 thereby trapping pushbutton spring 112 and pushbutton 106. The tool 62 can be released from the collet 100 by pressing the pushbutton 106 downward. This results in the collet 100 also being pushed downward such that the tapered fingers of the collet 100 expand radially outward, thereby releasing the grip on the tool 62. The upper bearing cap 110, via the bearing O-ring 114, compliantly supports the upper spindle bearing 66 in a radial direction. The upper bearing cap 110 also prevents upward axial movement of the upper spindle bearing 66.

The spindle chucking assembly 60 can be serviced or replaced by removing the upper end cap assembly 70. The upper end cap assembly 70 can be readily removed from the handpiece head 50 by rotating the upper threaded cap 108 in a counterclockwise direction relative to the head 50.

The lower cap assembly 68 and the various fluid transfer assemblies will be described with reference to FIGS. 4, 10, 11, 11A and 12. The lower end cap assembly 68 is threaded into the head 50 via mutually engaging threads 250. The lower end cap assembly 68 generally comprises a lower threaded cap 116, a preload spring 118, a lower spindle bearing 64, a bearing O-ring 115, an upper spray O-ring 120, a middle spray O-ring 122, and a lower spray O-ring 124.

Figure 11:
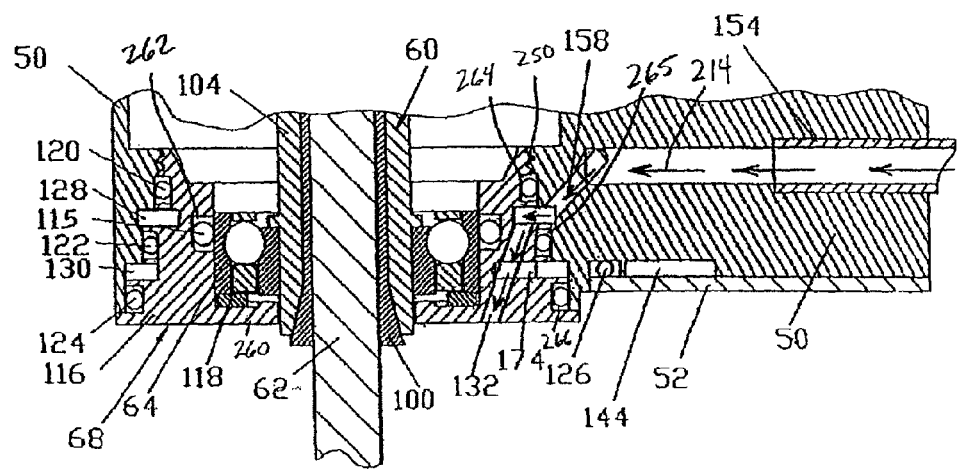
FIG. 11 is a side, multi-layer cross-sectional view of the head and lower handle portions of the electric handpiece of FIG. 3 illustrating the flow path of spray air to the air spray distribution chamber.
Figure 11A:
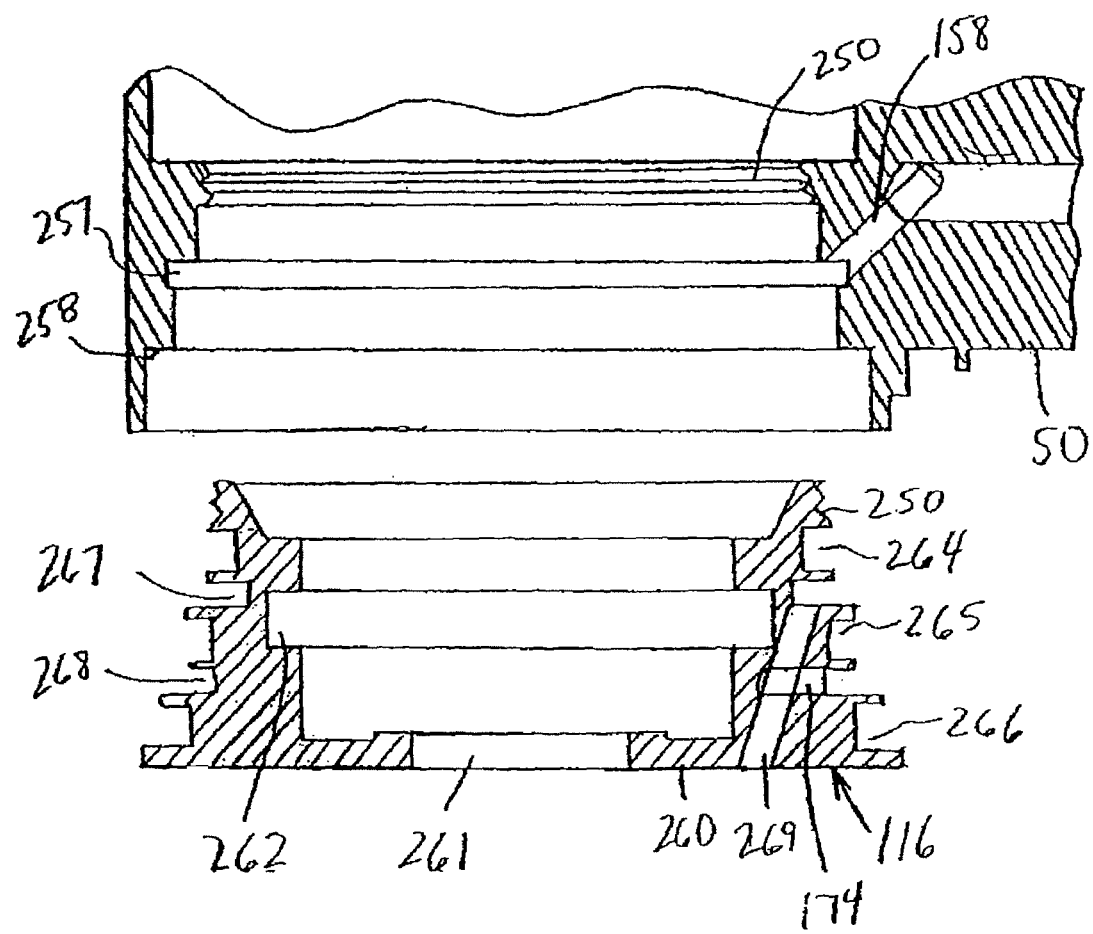
FIG. 11A is a side, multi-layer cross-sectional view similar to FIG. 11 prior to assembly of the lower cap to the handpiece head.

Referring to FIG. 11A, the lower threaded cap 116 and a portion of the head 50 are shown prior to assembly. The lower threaded cap 116 has a generally hollow body 260 with a opening 261 in a lower surface thereof for passage of the spindle shaft 104 therethrough. An internal circumferential groove 262 extends along the inside surface of the body 260 and is configured to receive and support the bearing O-ring 115. Three external circumferential grooves 264, 265, 266 extend along the outside surface of the body 260 and are configured to receive and support the upper spray O-ring 120, the middle spray O-ring 122, and the lower spray O-ring 124, respectively.

An upper circumferential distribution groove 267 extends along the outside surface of the body 260. The upper circumferential distribution groove 267 aligns with an internal circumferential distribution groove 257 extending along the inside surface of the head 50. The upper circumferential distribution groove 267 and the internal circumferential distribution groove 257 together define a circumferential spray distribution chamber 128, see FIG. 11, as will be described hereinafter.

A lower circumferential distribution groove 268 extends along the outside surface of the body 260. The lower circumferential distribution groove 268 aligns with an internal shoulder 258 extending along the inside surface of the head 50. The lower circumferential distribution groove 268 and the internal shoulder 258 together define a circumferential spray distribution chamber 130, see FIG. 11, as will be described hereinafter.

A series of spray nozzle holes 269 (only one shown in FIG. 11A) extend from the upper circumferential distribution groove 267 to the lower surface of body 260. Corresponding connecting holes 174 extend between each nozzle hole 269 and the lower circumferential distribution groove 268. The spray nozzle holes 269 define the spray nozzles 132, see FIG. 11, and receive fluid from the chambers defined by both circumferential distribution grooves 267 and 268.

Figure 12:
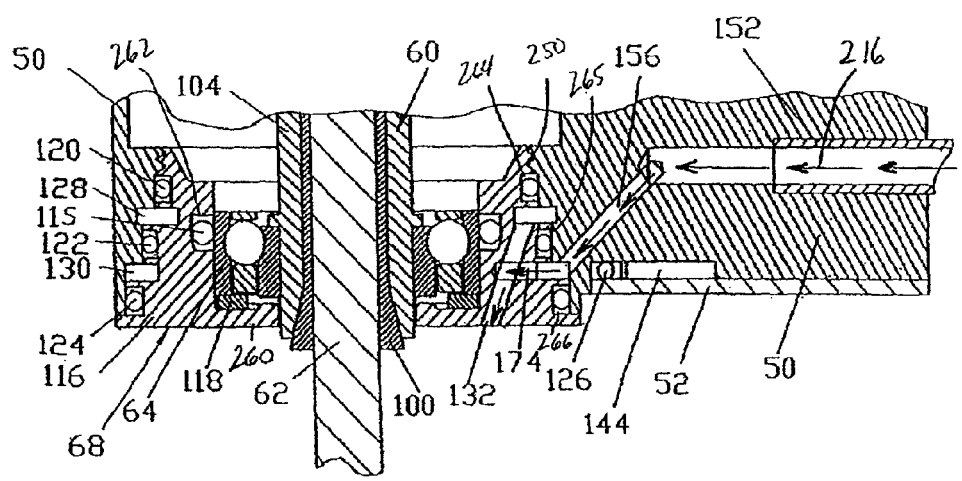
FIG. 12 is a side, multi-layer cross-sectional view similar to FIG. 11 illustrating the flow path of spray water to the water spray distribution chamber.

Referring to FIGS. 11 and 12, the bearing O-ring 115 is positioned in the groove 262 and the lower spindle bearing 64 is positioned in the interior of the lower cap 116 with the preload spring 118 positioned between the lower spindle bearing 64 and the lower surface of the lower cap body 260. The preload spring 118 forces the outer raceway of the lower spindle bearing 64 upward causing axial preloading of both the lower spindle bearing 64 and the upper spindle bearing 66. The bearing O-ring 114 acts as a compliant radial constraint for the outer raceway of the lower spindle bearing 64.

Air spray distribution chamber 128 is axially sealed by the upper spray O-ring 120 positioned in groove 264 and the middle spray O-ring 122 positioned in groove 265. Similarly, water spray distribution chamber 130 is axially sealed by the middle spray O-ring 122 and the lower spray O-ring 124 positioned in groove 266. A mixture of spray air and water is directed to the cutting tool 62 contact area on the tooth operative surface by multiple spray nozzles 132 (see FIG. 10). Spray air is supplied to each spray nozzle 132 by means of the air spray distribution chamber 128. Spray water is supplied to each spray nozzle 132 by means of the water spray distribution chamber 130 which supplies spray water into the spray water-nozzle connecting holes 174. The spray assembly will be described in more detail hereinafter.

For servicing any of the individual components in the lower end cap assembly 68, the lower threaded cap 116 is rotated in a counterclockwise direction relative to the head 50. Once the lower end cap assembly 68 is removed from the head 50, all individual components of the end cap 68 will able to be serviced or replaced.

Referring to FIGS. 10, 11, 13 and 14, the spray air and water mixture directed on to the cutting tool 62 via each of the spray nozzles 132 is supplied in separate spray air and water lines which originate in the dental delivery system 178.

Figure 10:
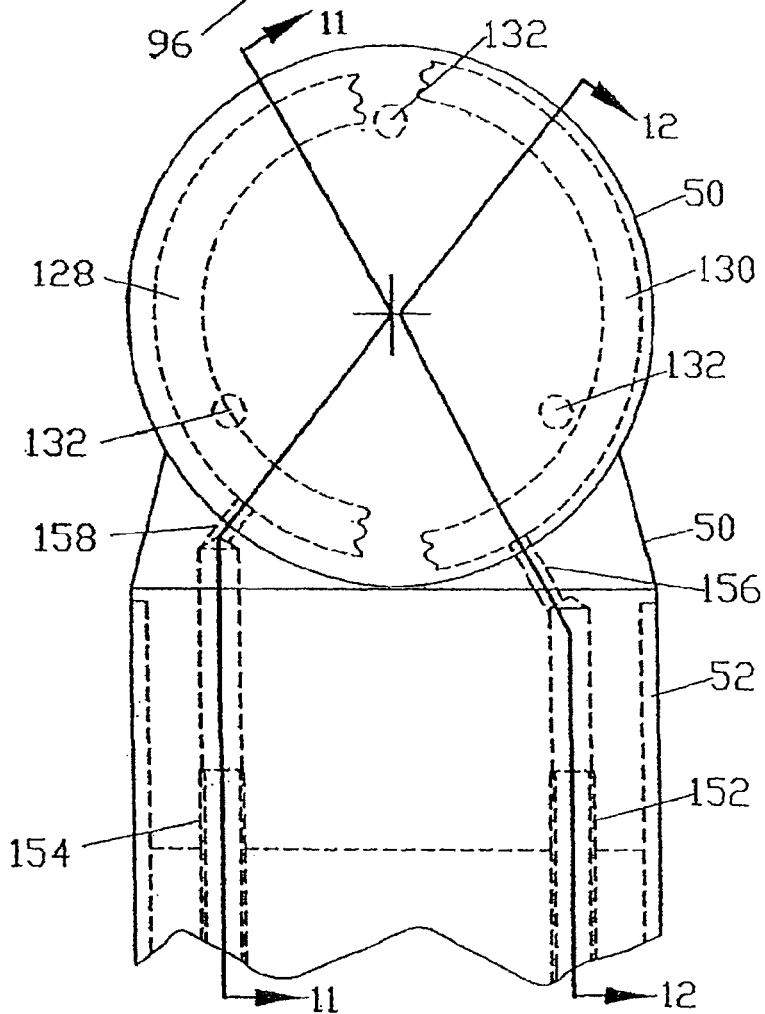
FIG. 10 is a top partial view of the head and lower handle portions showing the internal air and water spray lines.

Spray air flow 214 is directed from the dental delivery system 178 into a separate spray line 184 in the delivery hose 58. The spray air flow 214 is then delivered through the delivery hose adapter 56 and then through the sealing provision 166. The spray air flow 214 is next transferred to the air spray tube 154 which is essentially parallel to the cooling air tubes 134. The spray air tube 154 travels through the upper handle portion 54, through the lower handle portion 52 and then is finally attached to the head 50. FIG. 10 is a top view of the head 50 and its connection to lower handle portion 52. FIG. 11 is a multiple plane sectional view of the head 50 and lower end cap assembly 68. FIG. 11 has been provided to show the path of spray air flow 214 from the end of spray tube 154 toward its final destination at the exit of the multiple spray nozzles 132. After the spray air flow 214 leaves air spray tube 154, it continues through a hole in the head 50 until it intersects the air spray distribution chamber inlet hole 158 located in the head 50. The spray air distribution chamber inlet hole 158 is oriented along a compound angled axis and it terminates into air spray distribution chamber 128. Air distribution chamber 128 is a circular annular cavity which serves to divide the spray air flow 214 into multiple equal components for each of the multiple spray nozzles 132. Spray air flow 214 is then directed into the top segment of each spray nozzle 132 and then passes downward until it is joined by spray water flow 216 delivered by the spray water-nozzle connecting holes 174.

The path taken by spray water flow 216 is similar to the path taken by spray air flow 214. Spray water flow 216 is directed from the dental delivery system 178 into a separate spray water line 186 in the delivery hose 58. The spray water flow 216 is then delivered through the delivery hose adapter 56 and then through the sealing provision 166. The spray water flow 216 is then transferred to the spray water tube 152 which is also essentially parallel to the cooling air tubes 134. The water tube 152 travels through the upper handle portion 54 and then through the lower handle portion 52.

Referring to FIG. 10, the water tube 152 is then attached to head 50. FIG. 12 is a multiple plane sectional view of the head 50 and the lower end cap assembly 68 that has been provided to show the path of spray water flow 216 from the end of the spray water tube 152 toward its final destination at the exits of the multiple spray nozzles 132. After the spray water flow 216 leaves the water spray tube 152, it continues through a hole in the head 50 until it intersects the water spray distribution chamber inlet hole 156 located in the head 50. The spray water distribution chamber inlet hole 156 is oriented along a compound angled axis and it terminates in the water spray distribution chamber 130. The water distribution chamber 130 is a full circular annular cavity which serves to divide the spray water flow 216 into multiple equal components for each of the multiple spray water-nozzle connecting holes 174. Each of the multiple spray water-nozzle connection holes 174 is directed radially inward in the lower end cap 116 until each hole intersects a spray nozzle 132. The spray water flow 216 travels to the end of each spray water-nozzle connecting hole 174 where it is joined by spray air flow 214 which is already traveling downward from the upper half of spray nozzle 132.

The combined spray air and water mixture travels downward through the lower half of each spray nozzle 132 until it exits the bottom of the lower end cap 116. The resulting jet mixture of spray air flow 214 and spray water flow 216 then travels to the basic cutting zone of the cutting tool 62.

Referring to FIGS. 10, 11, 11A and 12, the minimum diameter of any spray air or water line in the entire electric handpiece 48 and delivery hose 58 system occurs in the multiple spray water-nozzle connecting holes 174. The spray water-nozzle connecting holes 174 can easily be accessed by simply removing the lower end cap assembly 68. Removing the lower end cap assembly 68 is accomplished by rotating the lower threaded cap 116 counterclockwise relative to the handpiece head 50. Each spray water-nozzle connecting hole 174 is easily accessible via groove 268 and can be readily cleaned with a small diameter drill bit mounted in a pin vise, or other suitable means.

The next increasing size hole that may become blocked occurs in the multiple spray nozzles 132. The lower end cap assembly 68 does not need to be removed to clean these holes. A small diameter drill bit mounted in a pin vise, or other suitable means, can be used to clean each hole of spray nozzle 132.

The water distribution chamber inlet hole 156 and the air distribution chamber inlet hole 158 are also relatively small in diameter. The lower end cap assembly 68 can be removed to gain access to both holes. A small diameter drill bit mounted in a pin vise, or other suitable means, can be used to clean the water distribution chamber inlet hole 156 and the air distribution chamber inlet hole 158.

The air and water distribution chambers 128 and 130 can be easily cleaned by removing the lower end cap assembly 68 and cleaning the respective grooves 267, 268 and 257 and the internal shoulder 258. Circumferential distribution chambers in prior art devices are typically not accessible for such cleaning.

The next larger restricting hole size that may become blocked occurs in several places in the handpiece 48 and delivery hose adapter 56. For this nominal hole size and larger, it is more practical to rely on water filter 198 to remove debris than it is to clear blockages after they occur. Water filter 198 is located on dental delivery system 178 and will filter all water delivered by the external water supply line 208. The filter screen should have a mesh hole diameter of about 50% of the nominal restricting hole diameter. Sizing the screen mesh in this manner will result in reliable filtering of particles greater than the nominal hole size and will result in a minimal pressure drop across water filter 198. Water filter 198 will prevent blockages in the water lines in the dental delivery system 178, the dental hose adapter 56 and the handpiece 48.

Referring to FIGS. 3 and 14, illumination of the work zone of cutting tool 62 is provided by an optional fiber optic light pipe 96 which is secured between the head 50 and the lower handle portion 52. The input end of the fiber optic light pipe 96 is illuminated by a light energy source 180 (not shown) contained within the delivery hose 58. One form of a light energy source 180 is a miniature lamp (not shown) in the delivery hose 58 interface with the handpiece 48. This lamp would be powered by electrical wires in the delivery hose 58 (not shown). Another light energy source 180 is a flexible fiber optic cable (not shown) which terminates at the delivery hose 58 interface with the handpiece 48. The flexible fiber optic cable would be powered by a focused lamp bulb (not shown) located in the dental delivery system 178. With any of these configurations, placement of the motor assembly 164 in the lower handle portion 52 allows the fiber optic light pipe 96 to extend along the central axis of the upper handle, thereby allowing a handpiece 48 with both a light source and a swivel connection. In the embodiment illustrated in FIG. 17, the light pipe is replaced by one or more LED lights 96' attached to the lower spindle cap 68'. The led lights 96' are preferably located around the spindle chuck which provides light without shadows. The LED lights 96' are attached to an electrical source and eliminate the need for the light energy source. The control system may maintain power to the lights 96' for an additional period, e.g. 10 seconds, so the dentist will have light even after the handpiece 48' is stopped.

With reference to FIG. 13, the physical relationship of the handpiece 48 and major supportive equipment will be described. The relationship for handpiece 48' will be similar and therefore is not described. The cutting tool 62 is chucked in the handpiece 48. The handpiece 48 is connected to the delivery hose 58 via the delivery hose adapter 56. The delivery hose 58 is connected to the dental delivery system 178. A foot pedal 192 is connected to the dental delivery system 178 via a foot pedal cord 200. The foot pedal 192 can be configured to send an electric, pneumatic or other signal to foot pedal cord 200. Foot pedal cord 200 can be respectively an electrical cord, a pneumatic cord (for example, a flexible elastomer tube assembly) or any other corresponding structure. The handpiece holder 202 is attached to the dental delivery system 178 and serves as the holding device for the handpiece 48 when it is not in use. A control panel 204, which is attached to the dental delivery system 178, will generally have one or more typical adjustment controls 206.

FIG. 14 shows the systematic relationship of the handpiece 48 and major supportive equipment. The relationship for handpiece 48' may be the same or may be operated in a different manner. The handpiece 48 is attached to the delivery hose 58 which is connected to the dental delivery system 178. The foot pedal 192 is connected to the dental delivery system via the foot pedal cord 200. The controller 194 is contained in the dental delivery system 178. The microprocessor 196 is electrically connected to the controller 194 via a microprocessor buss cable 182. An electrical relay 176 is electrically connected to the controller 194. If a pneumatic signal is used in foot pedal cord 200, a pressure signal device 190 is connected between one leg of the foot pedal cord 200 and the controller 194. If an electrical signal is used in foot pedal cord 200, the signal can be sent directly to the controller 194. The signal provided by the foot pedal 192 can be either digital (on-off) or analog for both electrical and pneumatic foot pedal cords 200.

The above describes the basic components of the handpiece 48. In view of the many applications of a dental handpiece and the widely varying optimum cutting tool speeds involved, the present invention further provides a system incorporating multiple handpieces 48 that cover the complete range of cutting tool speeds from approximately 70 RPM up to 220,000 RPM. In the preferred system, three handpieces 48 are included, with each of the three handpieces 48 employing a different winding to achieve maximum motor speeds of 40,000, 60,000 and 110,000 RPM.

Spindle and motor gear ratio variations and use of planetary gear stages in the motor have been selected to provide the entire 70 RPM to 220,000 RPM range. The following table summarizes the parameter differences among the three models.

| Model | Maximum RPM | Minimum RPM | Motor to Spindle Gear Ratio | Gearmotor Gear Ratio | Maximum Cutter RPM | Minimum Cutter RPM |
|---|---|---|---|---|---|---|
| Ultra Low | 40,000 | 2,800 | 1.61:1 (−) | 25:1 (−) | 1,000 | 70 |
| Low | 60,000 | 4,000 | 1.25:1 (+) | 5:1 (−) | 15,000 | 1,000 |
| High | 110,000 | 7,500 | 2:1 (+) | 1:1 (0) | 220,000 | 15,000 |

(+) indicates an increasing speed ratio
(−) indicates a decreasing speed ratio
(0) indicates no increasing or decreasing speed ratio Each electric handpiece 48 model covers approximately one third of the overall speed range. The only physical differences among the three improved electric models are the use of different configurations for motor gear 74, spindle gear 72 and the motor assembly 164. Motor gear 74 and mating spindle gear 72 vary as a matched set to either increase or decrease the rotational speed of cutting tool 62 relative to the nominal speed of motor shaft 76. Nominal speed requirements for motor shaft 76 for each of the three models have been attained by varying the configuration of motor windings 84. Additionally a single stage planetary gear reducing motor is used for the low speed model in order to reduce the speed of motor shaft 76 by a factor of five. The ultra low speed model uses a double stage planetary gear system to reduce the speed of motor shaft 76 by a factor of 25. The mounting face threads of motor housing 86, the diameter of the motor housing 86 and the diameter of motor shaft 76 are identical for the high speed and both lower speed models.

The above table provides an illustrative example of how different speed ranges can be obtained by utilizing different gear ratios and configuring the motor geometry to produce varying no load speeds. In the illustrated combination, three models of varying no load speeds and gear ratios are used to continuously cover the cutting tool 62 speed range from 75 RPM up to 220,000 RPM. The present invention is not limited to the specific combination illustrated. Various combinations of gear ratios and motor geometries can be selected to provide a desired range of speeds. Additionally, in the illustrated example, the minimum control RPM is set at about 7% of the maximum speed for a particular motor geometry. Again, the system is not limited to such other arrangements may also be utilized. For example, a motor controller may be selected to provide a lower minimum control RPM, thereby extending the continuous speed range even further.

A very significant advantage of the electric handpiece 48 is its ability to develop adequate torque at regulated speeds that are near the minimum of the speed range for each of the three models. The lack of sufficient lower speed torque is a major disadvantage of air powered handpieces.

To provide optimum motor control for each of the three handpiece models, the microprocessor 196 which instructs controller 194 has been designed to be capable of detecting which of the three handpiece models is in use. A resistance measurement check of the handpiece motor windings 84B and 84C is used to identify the model in use. A variation of the control scheme described earlier to detect an increase in electrical resistance of motor windings 84B and 84C for possible additional cooling air is used. Basically the microprocessor 196, which instructs controller 194, is programmed to perform a check of electrical resistance of motor windings 84B and 84C immediately after the microprocessor 196 detects depression of foot pedal 192. The resistance check only requires a few milliseconds. Following the resistance check, the microprocessor 196 energizes the electromagnetic relay coil 188 to switch the motor winding leads 88 from the "identify handpiece model" state to a "run motor" state. The microprocessor 196 then instructs the controller 194 to deliver varying voltage waveforms to the motor winding leads 88. The voltage waveforms are received by the motor windings 84 and result in the rotation of the motor shaft 76 and cutting tool 62.

This control scheme is practical because the nominal resistance of the windings of the three handpiece models varies significantly. Whenever a handpiece 48 is activated by depressing the foot pedal 192, the motor controller 194 circuitry quickly measures the winding resistance and compares it to a tabular range for each handpiece model. A tabular range has been calculated for each of the three windings to compensate for manufacturing winding tolerances. An allowance that compensates for the resistance change due to winding temperature from approximately 75 degrees F. up to about 212 degrees F. also has been added to the tabular range. The 75 degree F. limit is the motor winding temperature of a handpiece 48 which has been idle for several minutes. The 212 degree F. limit is the winding temperate of a handpiece which has been just removed from a steam autoclave.

Having described the components of the handpiece 48 and the system incorporating multiple handpiece models, an operational description is provided with reference to FIGS. 3, 4, 13 and 14.

Referring to FIG. 13, the electric handpiece 48 is illustrated as having a cutting tool 62 chucked in place and ready for use. The handpiece 48 has been removed from the handpiece holder 202 located on the dental delivery system 178. Water is supplied to the dental delivery system 178 via an external water supply line 208. Externally supplied water is filtered by a filter 198 located on the dental delivery system 178. The dental delivery system 178 is supplied compressed air via an external air supply line 210. Electricity is supplied to the dental delivery system 178 via an external electrical supply line 212. At this point, the handpiece 48 will not become operational until the dentist depresses the foot pedal 192.

FIG. 14 illustrates the same process state as depicted in FIG. 13, namely, the handpiece 48 is shown removed from the handpiece holder 202 and is ready to be used. When the dentist first depresses the foot pedal 192 connected to pneumatic foot pedal cord 200, a pneumatic signal is delivered from the foot pedal 192 via the foot pedal cord 200 to the pressure signal device 190. If an electrical foot pedal cord 200 is used, the electrical signal will be sent directly to controller 194. The pressure signal device 190 then sends an electrical signal to the controller 194 which relays the signal to the microprocessor 196 via the microprocessor buss cable 182. The microprocessor 196 determines that the foot pedal 192 has gone from a "not depressed" state to a "depressed" state. At this point, the microprocessor 196 postpones all output activity until it determines which handpiece 48 model has been connected to the delivery hose 58. The electrical relay 176 is currently in the "not energized" state shown in FIG. 14. At this point, the microprocessor 196 instructs the controller 194 to configure itself for a motor windings 84B and 84C resistance measurement check.

The controller 194 responds by delivering a fixed low level electrical current to resistance B terminal 44B with a return path via resistance C terminal 44C. The electrical current passing through motor windings 84B and 84C results in a voltage signal that is delivered to the controller 194 at resistance terminals 44B and 44C. The voltage signal is then passed on to the microprocessor 196 via the buss cable 182. The microprocessor 196 then compares the voltage signal to tabular voltage references which have been established in its memory. The reference voltages are directly proportional to the nominal resistances of motor windings 84B and 84C for each of the electric handpiece 48 models. The reference voltages are part of the fixed programming code of the microprocessor 196.

At this point, the microprocessor 196 will be able to determine which model of the handpiece 48 is attached to the delivery hose 58. Also, the microprocessor 196 will be able to detect the absence of the handpiece 48 and issue a warning alarm. After the microprocessor 196 successfully determines which handpiece model is attached to the delivery hose 58, the microprocessor 196 will then energize relay coil 188. This action transfers the motor winding leads 88 from resistance measuring terminals 44B and 44C to their corresponding power phase terminals 46A, 46B and 46C on the controller 194.

The microprocessor 196 will now instruct the controller 194 to deliver air, water, electrical power and light energy to the handpiece 48 via the delivery hose 58. Of all the preceding outputs delivered by the controller 194, electrical power to the motor assembly 164 is the only one that can be varied via the foot pedal 192. The foot pedal 192 does not directly control the electrical power or voltage delivered to the motor assembly 164. Instead, the foot pedal 192 is configured to send a variable signal which represents the desired rotational speed of the cutting tool 62. The signal varies approximately linearly to the amount of physical depression. Therefore, if the foot pedal 192 is depressed to half way of full travel, the signal will be approximately one half of the signal that occurs when the foot pedal 192 is fully depressed.

Another method of controlling speed of the rotating cutting tool 62 is to employ a desired cutter speed signaling device on control panel 204 on an accessible area or on an alternate readily viewable area. In this particular method, the foot pedal 192 is configured to send a digital on/off signal to microprocessor 196. Upon depression of the foot pedal 192, a digital on signal directs the microprocessor 196 to rotate the cutting tool 62 of the selected electrical handpiece. The rotation speed will be controlled by the microprocessor 196 in accordance with the desired cutter speed set on the speed signaling device on control panel 204 or elsewhere.

The shaft position sensor 90, mounted inside the motor assembly 164, detects the presence or absence of the shaft position reference device 160 located on the motor shaft 76. A corresponding electrical signal is sent via the shaft position sensor leads 94 to the controller 194. Based on this signal, the microprocessor 196 determines the present position and velocity of the motor shaft 76. The microprocessor 196 compares the desired speed signal generated by foot pedal 192 with the current speed signal of motor shaft 76. Depending on the difference between the desired and actual speeds, microprocessor 196 will issue electrical signals to controller 194. The signals are processed and amplified by controller 194 and are ultimately delivered to the individual motor windings 84A, 84B and 84C. This produces a circumferentially varying magnetic field in the motor windings 84. The magnetic field interacts with the MRM 82 and causes a circumferentially varying pattern of both attractive and repulsive forces operating on the MRM 82. The varying attractive and repulsive forces on the MRM 82 results in a torque being applied to motor shaft 76. The torque is then transmitted to the motor gear 74. A force is then transmitted to the spindle gear 72 located on the spindle chucking assembly 60. The transmitted force applied to spindle gear 72 causes a torque to be applied to the spindle chucking assembly 60. This results in a torque being applied to the cutting tool 62. Depending on the frictional opposing torques caused by the lower spindle bearing 64, upper spindle bearing 66 and the cutting surface in contact with the tooth, the cutting tool 62 will rotate at either a steady speed or a varying speed. The resulting speed information is continuously sensed by the shaft position sensor 90 and is delivered to the controller 194.

The microprocessor 196 also issues commands to the controller 194 to initiate air, water and light energy delivery to the handpiece 48. The air, water and light energy outputs delivered to the handpiece 48 by the controller 194 generally have rates that are not affected by the amount by which the foot pedal 192 is depressed. These outputs are delivered at fixed rates as soon as any amount of foot pedal 192 depression is detected by the microprocessor 196. However, some of the output rates can be manually varied by adjustments on the controller 194. Most typical adjustment controls 206 are normally placed on the control panel 204 of the dental delivery system 178 and can be readily accessed by dental personnel (see FIG. 13).

Light energy is delivered to the handpiece 48 via light energy source 180. The light energy is then delivered to the fiber optic light pipe 96 in the handpiece 48. A manual brightness level control may exist on the control panel 204. Also, the microprocessor 194 may be programmed to allow the light energy source 180 to remain on for a fixed or variable length of time after the foot pedal 192 is released.

Spray air flow 214 and spray water flow 216 are delivered from the controller 194 in unmixed form via spray air line 184 and water spray line 186 located in delivery hose 58. Individual manual adjustments of spray air flow 214 or spray water flow 216 can be made by typical adjustment controls 206 located on control panel 204 of the dental delivery system 178. Spray air flow 214 and spray water flow 216 are finally mixed together in each of the multiple spray nozzles 132 located on the lower portion of the head 50 of the handpiece 48. The spray air flow 214 and spray water flow 216 mixture exits each spray nozzle 132 and is then directed to the cutting tool 62 work zone.

Motor cooling air inlet flow 168 is also controlled by the microprocessor 196 commands to the controller 194. The flow rate of motor cooling inlet flow 168 is preferably not adjustable, but could be if desired. Motor cooling air inlet flow 168 is delivered to the handpiece 48 via the cooling air inlet line 140 of delivery hose 58. After cooling the motor assembly 164 and the lower handle portion 52 areas of the handpiece 48, the motor cooling air exhaust flow 170 is returned to the controller 194 via the exhaust air outlet line 142 of the delivery hose 58. Normally the exhaust flow is simply exhausted to atmosphere within the dental delivery system 178 housing. A muffler (not shown) may be employed to reduce exhaust noise.

As described earlier, particularly in cases where the handpiece 48 has been used for an extended period of time, it may be necessary to continue to supply motor cooling air inlet flow 168 following handpiece 48 usage. When the microprocessor 196 detects the foot pedal 192 is no longer depressed, it discontinues sending electrical signals that were previously processed and amplified by the controller 194 for delivery to the motor windings 84. The microprocessor 196 also terminates signals to the controller 194 which were previously used to activate spray air flow 214 and spray water flow 216 to the handpiece 48. The microprocessor 196 also instructs the controller 194 to terminate light energy flow 180 to the handpiece 48.

The microprocessor 196 does not immediately instruct the controller 194 to discontinue motor cooling air inlet flow 168 to the handpiece 48. Instead the microprocessor 196 instructs the controller 194 to remove energizing power from the electrical relay coil 188. This returns the electrical relay 176 to the not energized state shown in FIG. 14. The microprocessor 196 then waits several milliseconds for the relay coil 188 to become not energized. At this point, the microprocessor 196 instructs the controller 194 to configure itself to supply resistance measuring electrical signals to the microprocessor 196. The electrical signals received by the microprocessor 196 are indicative of the resistance of windings 84B and 84C in the handpiece 48. Details of using the measurement of motor winding 84B and 84C resistance to measure motor windings 84 temperature have been previously discussed. The microprocessor 196 continues to instruct the controller 194 to supply motor cooling air inlet flow 168 and continues to monitor the motor windings 84 resistance measuring signal. When the microprocessor 196 determines the motor windings 84 resistance has dropped to a level corresponding to an acceptable temperature, it instructs the controller 194 to discontinue supplying motor cooling inlet air flow 168 to the handpiece 48.

At this point, the microprocessor 196 places itself in a hold state where it continuously monitors the electrical signal supplied by the pressure signal device 190 to the controller 194. When the foot pedal 192 is depressed again, the microprocessor 196 senses the depression and repeats the handpiece 48 operative cycle discussed above.

While preferred embodiments of the invention have been shown and described herein, it will be understood that such embodiments are provided by way of example only. Numerous variations, changes and substitutions will occur to those skilled in the art without departing from the spirit of the invention. Accordingly, it is intended that the appended claims cover all such variations as fall within the spirit and scope of the invention.

What is claimed is:

1. An electric dental handpiece comprising:
   a head configured to rotatably support a tool;
   a handle defining a lower handle portion and an upper handle portion joined proximate to a rear gripping area of the handle, the lower handle portion engaging the head and the upper handle portion having an attachment area configured for attachment to a power supply, wherein a forward gripping area of the handle is defined proximate to the head, and
   an electric motor configured to rotate the tool is positioned with a majority thereof within the lower handle portion such that a center of gravity of the handpiece is within the lower handle portion.

2. The handpiece according to claim 1, wherein the center of gravity is positioned between the rear gripping area and the forward gripping area.

3. The handpiece according to claim 1 further comprising a spindle chucking assembly positioned in the head and configured to removably support the tool.

4. The handpiece according to claim 3, wherein the spindle chucking assembly includes a spindle gear configured to transfer a rotational force of the electric motor to the tool.

5. The handpiece according to claim 4, wherein the electric motor includes a motor shaft and a gear positioned on the motor shaft directly engages the spindle gear.

6. The handpiece according to claim 5, including a threaded connection between the motor and the head and wherein the threaded connection facilitates adjustment of the relative position of the spindle gear and the gear positioned on the motor shaft.

7. The handpiece according to claim 4, wherein the electric motor is associated with one or more speed reducing gears, the speed reducing gears having an output shaft with a gear thereon which directly engages the spindle gear.

8. The handpiece of claim 7, wherein the speed reducing gears provide a reduction ratio of between 5:1 and 25:1.

9. The handpiece of claim 5, wherein the spindle gear has a motor-to-spindle gear ratio of between 2:1 and 1:0.625.

10. The handpiece according to claim 1 further comprising one or more cooling air tubes for delivering a cooling air flow about the electric motor.

11. The handpiece according to claim 10, wherein the one or more cooling air tubes extend from the upper portion of the handle to the lower portion.

12. The handpiece according to claim 10 wherein the cooling air tubes are in communication with an air distribution chamber configured to generally reverse and diffuse the cooling air flow about the electric motor.

13. The handpiece according to claim 10, wherein the motor includes a motor housing enclosing a rotor and a stator and wherein the one or more cooling air tubes terminate at a rear end of the motor housing such that cooling air enters the motor housing and flows across the rotor and the stator.

14. The handpiece according to claim 13, wherein the motor housing includes at least one cooling air port at a forward end of the motor housing.

15. The handpiece according to claim 10 further comprising a temperature sensing mechanism for sensing a temperature of the electric motor.

16. The handpiece according to claim 15, wherein the electric motor includes at least one motor winding and the temperature sensing mechanism computes the temperature of the electric motor based on a measured resistance of the at least one motor winding.

17. The handpiece according to claim 15, wherein the cooling air flow to cool the electric motor is maintained, even after the motor is shut-off, if the temperature of the electric motor is greater than or equal to a predetermined threshold.

18. The handpiece according to claim 1, further comprising an optical fiber extending from the handle upper portion to the handle lower portion to illuminate an area proximate the tool, the optical fiber extending along a central axis of the upper handle portion adjacent the attachment area.

19. The handpiece according to claim 1, further comprising at least one LED light positioned on the head adjacent the tool.

20. The handpiece according to claim 19, wherein at least three LED lights are positioned on the head about the tool.

21. The handpiece according to claim 19, wherein an electrical control system is configured to continue powering the at least one LED light for a given period of time after power to the motor is stopped.

22. The electric dental handpiece according to claim 1 wherein the lower handle portion has a maximum outside diameter which is equal to or less than a maximum outside diameter of the upper handle.

\* \* \* \* \*